United States Patent
Kobayashi et al.

(10) Patent No.: US 12,377,196 B2
(45) Date of Patent: Aug. 5, 2025

(54) PREVENTING BIOLOGICAL TISSUE ADHESION

(71) Applicant: 3-D Matrix, Ltd., Tokyo (JP)

(72) Inventors: Satoru Kobayashi, Chigasaki (JP); Eun Seok Gil, Acton, MA (US); Lisa Spirio, S. Weymouth, MA (US)

(73) Assignee: 3-D Matrix, Ltd., Tokyo (JP)

( * ) Notice: Subject to any disclaimer, the term of this patent is extended or adjusted under 35 U.S.C. 154(b) by 0 days.

(21) Appl. No.: 18/167,864

(22) Filed: Feb. 12, 2023

(65) Prior Publication Data
US 2023/0241294 A1    Aug. 3, 2023

Related U.S. Application Data

(63) Continuation of application No. 17/519,638, filed on Nov. 5, 2021, now abandoned, which is a continuation of application No. 16/085,730, filed as application No. PCT/IB2017/000312 on Mar. 17, 2017, now abandoned.

(60) Provisional application No. 62/310,131, filed on Mar. 18, 2016, provisional application No. 62/310,121, filed on Mar. 18, 2016.

(51) Int. Cl.
*A61L 31/04*  (2006.01)
*A61L 31/14*  (2006.01)

(52) U.S. Cl.
CPC ........... *A61L 31/047* (2013.01); *A61L 31/043* (2013.01); *A61L 31/145* (2013.01)

(58) Field of Classification Search
CPC ...... A61L 31/047; A61L 31/145; A61L 31/16; A61P 41/00; A61P 29/00; A61P 25/04; A61P 15/00; A61P 1/00; A61B 2017/00823; A61B 2017/00893
See application file for complete search history.

(56) References Cited

U.S. PATENT DOCUMENTS

| | | | |
|---|---|---|---|
| 2006/0084607 A1 | 4/2006 | Spirio et al. | |
| 2008/0032934 A1* | 2/2008 | Ellis-Behnke | A61P 19/00 514/23 |
| 2014/0329914 A1 | 11/2014 | Kobayashi et al. | |

FOREIGN PATENT DOCUMENTS

| | | |
|---|---|---|
| CL | 201802643 | 4/2019 |
| CL | 201802644 | 7/2019 |
| WO | 2006014570 A1 | 2/2006 |
| WO | 2006014570 A2 | 2/2006 |
| WO | 2017158420 A1 | 9/2017 |

OTHER PUBLICATIONS

"Minutes of the Oral Proceedings," EP Application No. 17720563.0, dated Mar. 23, 2022 (3-D Matrix, Ltd.).
"Annex to the Communication," EP Application No. 17720563.0, dated Mar. 23, 2022 (3-D Matrix, Ltd.).
EPO Examination Report dated Nov. 11, 2019, Application No. EP 17720563.0 (3-D Matrix, Ltd.).
CL Office Action in Chilean Appln. No. 201802646, dated Feb. 14, 2020, 18 pages (with English translation).
International Search Report and Written Opinion in corresponding Application No. PCT/IB2017/000312 dated Jul. 26, 2017, pp. 1-12.
Rad-Malekshahi et al. "Biomedical Applications of Self-Assembling Peptides" (2016) Bioconjugate Chem. 27(1): 3-18.
Tokunaga et al. "Implantation of cardiac progenitor cells using self-assembling peptide improves cardiac function after myocardial infarction" (2010) Journal of Molecular and Cellular Cardiology 49(6): 972-983.
Zhang et al. "Designer self-assembling peptide nanofiber scaffolds for 3D tissue cell cultures" (2005) Seminars in Cancer Biology 15: 413-420.
Rajab et al., "A Direct Comparison of Seprafilm, Adept, Intercoat, and Spraygel for Adhesion Prophylaxis," J. Surg. Res. 2010; 161(2): 246-249.
Tang et al., "Peritoneal adhesions: Occurrence, prevention and experimental models," Acta Biomaterialia, 2020; 116: 84-104.
Hermans, Michel H.E., et al., "Adhesion prevention in an intraperitoneal wound model: Performance of two resorbable hemostats in a controlled study in rabbits", J Bilomed Materials Res Part B 2012:100B:1621-1626.
Hoffmann, Nathan E., et al., "Choice of Hemostatic Agent Ifluences Adhesion Formation in a Ract Cecal Adhesion Model", Journal of Surgical Research, 1-5 (2009) doi: 10.1016/j.jss.2008.08.008.
Menzies, Donald, et al., "Intestinal obstruction from adhesions—how big is the problem?", Annals of the Royal College of Surgeons of England, vol. 72, pp. 6-63, (1990).
Okabayashi, Koji, et al., "Adhesions after abdominal surgery: a systematic review of the incidence, distribution and severity", Surgery Today, Springer, Japan; May 9, 2013, DOI 10.1007/s00595-013-0591-8.
Rodgers, Kathleen, et al., "Evaluation of polyethylene glycol/polylactic acid films in the prevention of adhesions in the rabbit adhesion formation and reformation sidewall models", Vertility and Sterility, vol. 69, No. 3, Mar. 1998, American Society for Reproductive Medicine, Published by Elsevier Science Inc. (1997).
Yeo, Yoon et al., "Prevention of peritoneal adhesions with an in situ cross-linkable hyaluronan hydrogel delivering budesonide", Journal of Controlled Release 120 (2007) 178-185.

* cited by examiner

*Primary Examiner* — Sudhakar Katakam
(74) *Attorney, Agent, or Firm* — Supra, PLLC; Beth L. Smiley; Constantine M. Linnik

(57) ABSTRACT

Methods and materials for mitigating biological tissue adhesion are described herein. One method for mitigating adhesion to a biological tissue includes administering an effective amount of a self-assembling peptide solution to the biological tissue, wherein the self-assembling peptide is between about 7 amino acids and 32 amino acids in length and the self-assembling peptide solution forms a hydrogel under physiological conditions.

8 Claims, No Drawings

Specification includes a Sequence Listing.

PREVENTING BIOLOGICAL TISSUE ADHESION

CONTINUITY

This application is a continuation of U.S. patent application Ser. No. 17/519,638, filed Nov. 5, 2021, which is a continuation of U.S. patent application Ser. No. 16/085,730, filed Sep. 17, 2018, which is a National Stage Entry of International Application No. PCT/IB2017/000312, filed Mar. 17, 2017, which claims priority to U.S. provisional Application Nos. 62/310,121 and 62/310,131, both filed Mar. 18, 2016, each of which is expressly incorporated herein by reference.

SEQUENCE LISTING

The instant application contains an XML Sequence Listing which is being submitted electronically and is hereby incorporated by reference in its entirety. Said Sequence Listing, created on Feb. 12, 2023 (EST), is named 3DM-R0001_US06-SLA.xml and is 110,499 bytes in size.

FIELD OF THE INVENTION

This disclosure relates to materials and methods that may be used in medical, research, and industrial applications. More particularly, this disclosure relates to materials and methods that may be used to promote anti-adhesion, for example by preventing or mitigating biological tissue adhesion.

BACKGROUND

Postoperative tissue adhesion occurs in connection with various procedures such as those in neurosurgery, thoracic surgery, urology, obstetrics, gynecology, digestive system surgery and orthopedic surgery. Adhesion generally relates to a physiological and biological repair reaction. It is considered difficult to prevent such adhesion completely, though the nature of adhesion may vary between different tissues.

Currently, sodium hyaluronate, carboxymethyl cellulose, oxidized regenerated cellulose, and expanded polytetrafluoroethylene (ePTFE) are used clinically as anti-adhesion materials. However, these materials may have limited efficacy and/or side effects and/or are difficult to use. For example, such materials are commonly provided in sheet form, which may be difficult to immobilize at the application site. They also may be difficult to use during endoscopic surgeries and cannot necessarily be effectively applied to bleeding sites.

Accordingly, there remains a need for improved treatments for preventing or mitigating biological tissue adhesion.

SUMMARY

The invention is based, at least in part, upon the discovery that certain amphiphilic peptide solutions can be surprisingly and advantageously used for preventing or mitigating biological tissue adhesion.

In various aspects, the invention provides a method for mitigating adhesion to a biological tissue, the method comprising administering an effective amount of a self-assembling peptide solution to the biological tissue, wherein the self-assembling peptide is between about 7 amino acids and 32 amino acids in length and the self-assembling peptide solution forms a hydrogel under physiological conditions, and wherein the hydrogel mitigates adhesion to the biological tissue.

In various aspects, the invention provides a method for mitigating adhesion between biological tissue, the method comprising administering an effective amount of a self-assembling peptide solution to a biological tissue at a surgical site, wherein the self-assembling peptide is between about 7 amino acids and 32 amino acids in length and the self-assembling peptide solution forms a hydrogel under physiological conditions, and wherein the hydrogel mitigates adhesion of another biological tissue to the biological tissue at the surgical site.

In various aspects, the invention provides a use of an effective amount of a self-assembling peptide solution for mitigating adhesion to a biological tissue, wherein the self-assembling peptide is between about 7 amino acids and 32 amino acids in length and the self-assembling peptide solution forms a hydrogel under physiological conditions, and wherein the hydrogel mitigates adhesion to the biological tissue.

In various aspects, the invention provides a use of an effective amount of a self-assembling peptide solution for mitigating adhesion to a biological tissue, wherein the self-assembling peptide is between about 7 amino acids and 32 amino acids in length and the self-assembling peptide solution forms a hydrogel under physiological conditions, and wherein the hydrogel mitigates adhesion of another biological tissue to the biological tissue at the surgical site.

In various aspects, the invention provides a method of promoting anti-adhesion, comprising: introducing a delivery device to a target area; positioning an end of the delivery device in the target area at which anti-adhesion is desired; administering through the delivery device a solution comprising a self-assembling peptide comprising between about 7 amino acids and 32 amino acids in an effective amount and in an effective concentration to the target area to form a hydrogel under physiological conditions of the target area to promote anti-adhesion; and removing the delivery device from the target area.

In various aspects, the invention provides a composition comprising a self-assembling peptide comprising between about 7 amino acids and 32 amino acids in an effective amount and in an effective concentration for use in forming a hydrogel under physiological conditions to promote anti-adhesion.

In various aspects, the invention provides a kit for promoting anti-adhesion, comprising a self-assembling peptide comprising between about 7 amino acids and about 32 amino acids in an effective amount to form a hydrogel under physiological conditions to promote anti-adhesion and instructions for administering the self-assembling peptide to a target area.

In various aspects, the invention provides a method of promoting anti-adhesion in epicardial ablation, comprising introducing a delivery device to a target area associated with the epicardial ablation, positioning an end of the delivery device in the target area at which anti-adhesion is desired, administering through the delivery device a solution comprising a self-assembling peptide comprising between about 7 amino acids and 32 amino acids in an effective amount and in an effective concentration to the target area to form a hydrogel under physiological conditions of the target area to promote anti-adhesion, and removing the delivery device from the target area.

In various aspects, the invention provides a kit for promoting anti-adhesion in epicardial ablation, comprising a self-assembling peptide comprising between about 7 amino acids and about 32 amino acids in an effective amount to form a hydrogel under physiological conditions to promote anti-adhesion and instructions for administering the self-assembling peptide to a target area associated with epicardial ablation.

In various aspects, the invention provides a method of facilitating promotion of anti-adhesion in epicardial ablation, comprising: providing a solution comprising a self-assembling peptide comprising between about 7 amino acids to about 32 amino acids in an effective amount and in an effective concentration to form a hydrogel in a target area associated with the epicardial ablation under physiological conditions to promote anti-adhesion; and providing instructions for administering the solution to the target area through introduction of the solution through a delivery device positioned in the target area.

In various aspects, the invention provides a macroscopic scaffold consisting essentially of a plurality of self-assembling peptides, each of the self-assembling peptides comprising between about 7 amino acids and about 32 amino acids in an effective amount that is capable of being positioned within a target area associated with epicardial ablation to promote anti-adhesion.

As will be understood by those skilled in the art, any of the aspects above can be combined with any one or more of the features below.

In various embodiments, the biological tissue comprises an epicardium.

In various embodiments, the biological tissue comprises an epicardium subjected to ablation, preferably ventricular tachycardia ablation.

In various embodiments, the self-assembling peptide comprises about 12 to about 16 amino acids that alternate between hydrophobic and a hydrophilic amino acids.

In various embodiments, the self-assembling peptide comprises a sequence selected from RADA (SEQ ID NO:1), IEIK (SEQ ID NO:2), TTTT (SEQ ID NO:3), ATAT (SEQ ID NO:4), TVTV (SEQ ID NO:5), ASAS (SEQ ID NO:6), SSSS (SEQ ID NO:7), VVVTTTT (SEQ ID NO:8), and a combination thereof. In various embodiments, the self-assembling peptide comprises a sequence selected from $(RADA)_4$ (SEQ ID NO:11), $(IEIK)_3I$ (SEQ ID NO:12), and $(KLDL)_3$ (SEQ ID NO:14).

In various embodiments, the self-assembling peptide is about 0.1 to about 10 w/v % of the solution or about 0.1 to about 3.5 w/v % of the solution.

In various embodiments, the self-assembling peptide is about 1, about 2.5, or about 3 w/v % of the solution.

In various embodiments, the effective amount is approximately 0.1 mL per 1 $cm^2$ to approximately 5 mL per 1 $cm^2$ of target area.

In various embodiments, the effective amount is approximately 1 mL per 1 $cm^2$ of target area.

In various embodiments, the hydrogel is formed before administering the self-assembling peptide solution to target area.

In various embodiments, the hydrogel is formed after administering the self-assembling peptide solution to target area.

In various embodiments, the solution further comprises a biologically active agent.

In various embodiments, the solution is substantially free of cells and/or drugs.

In various embodiments, the self-assembling peptide solution is administered in vivo.

In various embodiments, the biological tissue is a human tissue.

In various embodiments, the solution is an aqueous solution and wherein a concentration of the peptide in the aqueous solution is about 0.1 weight per volume (w/v) percent to about 3 w/v percent.

In various embodiments, the method further comprises visualizing the target area prior to introducing and/or subsequent to removing the delivery device from the target area.

In various embodiments, the method further comprises monitoring the target area after removing the delivery device.

In various embodiments, the method further comprises preparing the solution comprising the self-assembling peptide.

In various embodiments, the target site relates to a catheter approach to epicardial ablation.

In various embodiments, the target site is a surgical site.

In various embodiments, the hydrogel treats, prevents, and/or mitigates intra-abdominal adhesion formation.

In various embodiments, biological tissue comprises intraperitoneum, cecum, intestine, preferentially large intestine, and/or colon.

In various embodiments, hydrogel treats, prevents, and/or mitigates pelvic adhesion formation.

In various embodiments, hydrogel treats, prevents, and/or mitigates adhesion formation in an obstetric or gynecologic procedure.

In various embodiments, obstetric or gynecologic procedure comprises cesarean delivery, abdominal hysterectomy, preferentially myomectomy, ovarian cystectomy, or surgery for an invasive gynecologic malignancy.

In various embodiments, treating, preventing, and/or mitigating adhesion formation treats, prevents, and/or mitigates small bowel obstruction, infertility, chronic pain, and dyspareunia.

These and other advantages of the present technology will be apparent when reference is made to the following description.

DETAILED DESCRIPTION

The invention is based, at least in part, upon the discovery that certain amphiphilic peptide solutions can be surprisingly and advantageously used to mitigate biological tissue adhesion.

Broadly, the methods and materials may employ a hydrogel barrier for preventing or mitigating biological tissue adhesion. The mitigation may be partial or complete. The materials and methods may include administration, application, or injection of a self-assembling peptide, or a solution comprising a self-assembling peptide, or a composition comprising a self-assembling peptide, to a predetermined or desired target area, thereby preventing or mitigating biological tissue adhesion.

For example, in various aspects and embodiments, the invention provides methods and materials for mitigating adhesion to a biological tissue. The method includes administering an effective amount of a self-assembling peptide solution to the biological tissue, where the self-assembling peptide is between about 7 amino acids and 32 amino acids in length and the self-assembling peptide solution forms a hydrogel under physiological conditions. In certain embodiments, the adhesion is between two biological tissues. In other certain embodiments, the biological tissue may comprise an epicardium. In yet other certain embodiments, the biological tissue may comprise an epicardium subjected to ablation. In further other certain embodiments, the biological tissue may comprise an epicardium subjected to ventricular tachycardia ablation.

Through administration of the solution comprising the self-assembling peptide, a hydrogel barrier may be formed. The hydrogel barrier may be formed in the target area to promote anti-adhesion. The self-organizing or self-assembling peptides of the present disclosure may include application of the self-organizing or self-assembling peptides to a predetermined or desired target. The self-organizing or self-assembling peptide may be applied or introduced to a target site in the form of a peptide solution, hydrogel, membrane or other form. A target site may be a predetermined area of a subject that requires a particular treatment. In some embodiments, the target site may relate to a surgical site, such as an endoscopic surgical site. In other embodiments, the target site may be a bleeding site.

Various features of the invention are discussed, in turn, below.

As used herein, the term "subject" is intended to include human and non-human animals, for example, vertebrates, large animals, and primates. In certain embodiments, the subject is a mammalian subject, and in particular embodiments, the subject is a human subject. Although applications with humans are clearly foreseen, veterinary applications, for example, with non-human animals, are also envisaged herein. The term "non-human animals" of the invention includes all vertebrates, for example, non-mammals (such as birds, for example, chickens; amphibians; reptiles) and mammals, such as non-human primates, domesticated, and agriculturally useful animals, for example, sheep, dog, cat, cow, pig, rat, among others.

The term "self-assembling peptide" may refer to a peptide comprising a self-assembling motif. Self-assembling peptides are peptides that are capable of self-assembly into structures including but not limited to, macroscopic membranes or nanostructures. For example, the self-assembling peptide may exhibit a beta-sheet structure in aqueous solution in the presence of specific conditions to induce the beta-sheet structure. These specific conditions may include adjusting the pH of a self-assembling peptide solution. The adjustment may be an increase or a decrease in the pH of the self-assembling peptide solution. The increase in pH may be an increase in pH to a physiological pH. The specific conditions may also include adding a cation, such as a monovalent cation, to a self-assembling peptide solution. The specific conditions may include conditions related to the pancreas. The self-assembling peptides may be referred to as or be a part of a composition, peptide solution, peptide powder, hydrogel, or scaffold. The self-assembling peptide may be administered to a target area in the form of a peptide solution, composition, hydrogel, membrane, scaffold or other form.

During self-organization or self-assembly, the peptide may form nanofibers. The self-organization or self-assembly may cause gelling of the peptide in solution. The gelling may provide or form a hydrogel. The peptide may form a beta-sheet spontaneously in the solution under the physiological pH level. The peptide may form a beta-sheet spontaneously in the solution under physiological conditions and/or in the presence of a cation.

The term "hydrogel" may refer to a material that is comprised of a polymer and a high percentage of water, for example, at least 90% water.

The self-assembling peptide may be an amphiphilic self-assembling peptide. By "amphiphilic" it is meant that the peptide comprises hydrophobic portions and hydrophilic portions. In some embodiments, an amphiphilic peptide may comprise, consist essentially of, or consist of alternating hydrophobic amino acids and hydrophilic amino acids. By alternating, it is meant to include a series of three or more amino acids that alternate between a hydrophobic amino acid and a hydrophilic amino acid, and it need not include each and every amino acid in the peptide sequence alternating between a hydrophobic and a hydrophilic amino acid. In certain embodiments, the peptide may comprise a first portion that is amphiphilic and a second portion that is not amphiphilic.

The self-assembling peptide, also referred to herein as "peptide" or "self-assembling oligopeptides," may be administered to the pre-determined or desired target area in the form of a self-assembling peptide solution, composition, hydrogel, membrane, scaffold or other form. The hydrogel may also be referred to as a membrane or scaffold throughout this disclosure.

The pre-determined or desired target area may be biological tissue. The pre-determined or desired target area may be at or near the location of a surgery. The pre-determined or desired target area may be established based on the site of or other area that may have undergone a surgical procedure, or an unintentional or intentional trauma. In some embodiments, the target site may be an epicardium. In some other embodiments, the target site may be an epicardium subjected to ablation. In further some other embodiments, the target site may be an epicardium subjected to ventricular tachycardia ablation. In various embodiments, the target site comprises intraperitoneum, cecum, intestine, preferentially large intestine, and/or colon. In various embodiments, the target site comprises a biological tissue subject to cesarean delivery, abdominal hysterectomy, preferentially myomectomy, ovarian cystectomy, or surgery for an invasive gynecologic malignancy.

The self-assembling peptide solution may be an aqueous self-assembling peptide solution. The self-assembling peptide may be administered, applied, or injected in a solution that is substantially cell-free, or free of cells. In certain embodiments, the self-assembling peptide may be administered, applied, or injected in a solution that is cell-free or free of cells.

The self-assembling peptide may also be administered, applied, or injected in a solution that is substantially drug-free or free of drugs. In certain embodiments, the self-assembling peptide may be administered, applied, or injected in a solution that is drug-free or free of drugs. In certain other embodiments, the self-assembling peptide may be administered, applied, or injected in a solution that is substantially cell-free and substantially drug-free. In still further certain other embodiments, the self-assembling peptide may be administered, applied, or injected in a solution that is cell-free and drug-free.

The self-assembling peptide solution may comprise, consist of, or consist essentially of the self-assembling peptide. The self-assembling peptide may be in a modified or unmodified form. By modified, it is meant that the self-assembling peptide may have one or more domains that comprise one or more amino acids that, when provided in solution by itself, would not self-assemble. By unmodified, it is meant that the self-assembling peptide may not have any other domains other than those that provide for self-assembly of the peptide. That is, an unmodified peptide consists of alternating hydrophobic and hydrophilic amino acids that may self-assemble into a beta-sheet, or a macroscopic structure, such as a hydrogel.

The self-assembling peptide can be at least about 7 amino acids, between about 7 and 32 amino acids, or between about 12 and 16 amino acids. Other peptides that do not comprise, consist of, or consist essentially of at least about 7 amino acids may be contemplated by this disclosure. The self-assembling peptides may be composed of about 6 to about 200 amino acid residues. In certain embodiments, about 8 to about 32 residues may be used in the self-assembling peptides, while in other embodiments self-assembling peptides may have about 7 to about 17 residues. In certain other examples, the self-assembling peptides may be peptides of at least 8 amino acids, at least about 12 amino acids, or at least about 16 amino acids.

The materials and methods may comprise administering a self-assembling peptide to a predetermined or desired target. The peptide may be administered as a hydrogel or form a hydrogel upon administration. A hydrogel is a term that may refer to a colloidal gel that is dispersed in water. The hydrogel may also be referred to as a membrane or scaffold throughout this disclosure. The systems and methods may also comprise applying a self-assembling peptide to a predetermined or desired target as a solution such as an aqueous peptide solution.

The term "administering," is intended to include, but is not limited to, applying, introducing or injecting the self-assembling peptide, in one or more of various forms including, but not limited to, by itself, by way of solution, such as an aqueous solution, or by way of a composition, hydrogel, or scaffold, with or without additional components.

The method may comprise introducing a delivery device at or near a predetermined or desired target area of a subject. The method may comprise introducing a delivery device comprising at least one of a syringe, tube, pipette, catheter, catheter syringe, or other needle-based device to the predetermined or desired target area of a subject. The self-assembling peptide may be administered by way of a syringe, tube, pipette, catheter, catheter syringe, or other needle-based device to the predetermined or desired target area of a subject. The gauge of the syringe needle may be selected to provide an adequate flow of a composition, a solution, a hydrogel, or a liquid from the syringe to the target area. This may be based in some embodiments on at least one of the amount of self-assembling peptide in a composition, peptide solution, or a hydrogel being administered, the concentration of the peptide solution, in the composition, or the hydrogel, and the viscosity of the peptide solution, composition, or hydrogel. The delivery device may be a conventional device or designed to accomplish at least one of to reach a specific target area, achieve a specific dosing regime, deliver a specific target volume, amount, or concentration, and deliver accurately to a target area.

The method of mitigating biological tissue adhesion may comprise introducing a delivery device into the subject and positioning an end of the delivery device in a predetermined or target area, such as a portion of a surgical site. The self-assembling peptide may be administered by way of a delivery device to the target area in which at least is desired. The use of a delivery device may provide a more selective administration of the peptide to provide for a more accurate delivery to the target area. Selective administration of the peptide may allow for enhanced and more targeted delivery of the peptide solution, composition, or hydrogel such that it is successful and positioned in the desired location in an accurate manner. The selective administration may provide enhanced, targeted delivery that markedly improves the positioning and effectiveness of the treatment over use of another delivery device. Delivery devices that may be used in the systems, methods, and kits of the disclosure may include a syringe, tube, needle, pipette, syringe catheter, other needle-based device, or catheter.

Use of a delivery device, such as a catheter, may include use of accompanying devices, such as a guidewire used to guide the catheter into position, or an endoscope that may allow proper placement of the catheter and visualization of the target area, and/or the path to the target area. The endoscope may be a tube that may comprise at least one of a light and a camera or other visualization device to allow images of the subject's body to be viewed. The guidewire or endoscope may be introduced into the subject, for example, by way of an incision in the skin. The endoscope may be introduced to the target area prior to introducing the delivery device to the target area.

The use of the delivery device, such as a syringe, tube, needle, pipette, syringe catheter, other needle-based device, catheter, or endoscope may require determining the diameter or size of the opening in which there is a target area, such that at least a portion of the syringe, tube, needle, pipette, syringe catheter, other needle-type device, catheter, or endoscope may enter the opening to administer the peptide, peptide solution, composition, or hydrogel to the target area.

In certain embodiments, the hydrogel may be formed in vitro and administered to the desired location in vivo. In certain examples, this location may be the target area. In other examples, this location may be upstream, downstream of the area, or substantially near the area. It may be desired to allow a migration of the hydrogel to the area in which it is desired. Alternatively, another procedure may position the hydrogel in the area in which it is desired. The desired location or target area may be at least a portion of an area in which it is desired to provide or promote anti-adhesion, e.g., prevent or mitigate biological tissue adhesion, in a subject.

In certain aspects of the disclosure, the hydrogel may be formed in vivo. A solution comprising the self-assembling peptide, such as an aqueous solution, may be inserted to an in vivo location or area of a subject to provide or promote anti-adhesion, e.g., prevent or mitigate biological tissue adhesion, in a subject. In certain examples, the hydrogel may be formed in vivo at one location, and allowed to migrate to the area in which it is desired to provide or promote anti-adhesion, e.g., prevent or mitigate biological tissue adhesion, in a subject. Alternatively, another procedure may place the hydrogel in the area in which it is desired to provide or promote anti-adhesion, e.g., prevent or mitigate biological tissue adhesion, in a subject. The peptides of the present disclosure may be in the form of a powder, a solution, a gel, or the like. Since the self-assembling peptide gels in response to changes in solution pH and salt concentration, it can be distributed as a liquid that gels upon contact with a subject during application or administration.

In certain environments, the peptide solution may be a weak hydrogel and, as a result, it may be administered by way of a delivery device as described herein.

In accordance with some embodiments, the self-assembling peptides may be amphiphilic, alternating between hydrophobic amino acids and hydrophilic amino acids.

In accordance with one or more embodiments, a subject may be evaluated to determine a need to provide or promote anti-adhesion, e.g., prevent or mitigate biological tissue adhesion, in a subject. Once the evaluation has been completed, a peptide solution to administer to the subject may be prepared.

In some embodiments, a biologically active agent may be used with the materials and methods of the present disclosure. A biologically active agent may comprise a compound, including a peptide, DNA sequence, chemical compound, or inorganic or organic compound that may impart some activity, regulation, modulation, or adjustment of a condition or other activity in a subject or in a laboratory setting. The biologically active agent may interact with another component to provide such activity. The biologically active agent may be referred to as a drug in accordance with some embodiments herein. In certain embodiments, one or more biologically active agents may be gradually released to the outside of the peptide system. For example, the one or more biologically active agents may be gradually released from the hydrogel. Both in vitro and in vivo testing has demonstrated this gradual release of a biologically active agent. The biologically active agent may be added to the peptide solution prior to administering to a subject, or may be administered separately from the solution to the subject. The one or more biologically active agents may be encapsulated within the system, for example, they may be encapsulated in the hydrogel, solution, or nanofibers.

The self-assembling peptides may exhibit a beta-sheet structure in aqueous solution in the presence of physiological pH and/or a cation, such as a monovalent cation, or other conditions applicable to a surgical site.

The peptides may be generally stable in aqueous solutions and self-assemble into large, macroscopic structures, scaffolds, or matrices when exposed to physiological conditions, physiological pH, or physiological levels of salt. Once the hydrogel is formed it may not decompose, or may decompose or biodegrade after a period of time. The rate of decomposition may be based at least in part on at least one of the amino acid sequence and conditions of its surroundings.

By "macroscopic" it is meant as having dimensions large enough to be visible under magnification of 10-fold or less. In preferred embodiments, a macroscopic structure is visible to the naked eye. A macroscopic structure may be transparent and may be two-dimensional, or three-dimensional. Typically each dimension is at least 10 µm, in size. In certain embodiments, at least two dimensions are at least 100 µm, or at least 1000 µm in size. Frequently at least two dimensions are at least 1-10 mm in size, 10-100 mm in size, or more. In certain embodiments, the size of the filaments may be about 10 nanometers (nm) to about 20 nm. The interfilament distance may be about 50 nm to about 80 nm. The self-assembling peptides of the present disclosure may have a length of about 5 nm. The self-assembling peptides of the present disclosure may have a nanofiber diameter in a range of about 10 nm to about 20 nm and an average pore size is in a range of about 5 nm to about 200 nm. In certain embodiments, the nanofiber diameter, the pore size, and the nanofiber density may be controlled by at least one of the concentration of peptide solution used and the amount of peptide solution used, such as the volume of peptide solution. As such, at least one of a specific concentration of peptide in solution and a specific amount of peptide solution to provide at least one of a desired nanofiber diameter, pore size, and density to adequately provide for anti-adhesion may be selected.

"Physiological conditions" may occur in nature for a particular organism, cell system, or subject which may be in contrast to artificial laboratory conditions. The conditions may comprise one or more properties such as one or more particular properties or one or more ranges of properties. For example, the physiological conditions may include a temperature or range of temperatures, a pH or range of pH's, a pressure or range of pressures, and one or more concentrations of particular compounds, salts, and other components.

For example, in some examples, the physiological conditions may include a temperature in a range of about 20 to about 40 degrees Celsius. In some examples, the atmospheric pressure may be about 1 atm. The pH may be in the range of a physiological pH. For example, the pH may be in a range of about 6 to about 8. The physiological conditions may include cations such as monovalent metal cations that may induce membrane or hydrogel formation. These may include sodium chloride (NaCl). The physiological conditions may also include a glucose concentration, sucrose concentration, or other sugar concentration, of between about 1 mM and about 20 mM.

The peptides may also be complementary and structurally compatible. Complementary refers to the ability of the peptides to interact through ionized pairs and/or hydrogen bonds which form between their hydrophilic side-chains, and structurally compatible refers to the ability of complementary peptides to maintain a constant distance between their peptide backbones. Peptides having these properties participate in intermolecular interactions which result in the formation and stabilization of beta-sheets at the secondary structure level and interwoven filaments at the tertiary structure level.

Both homogeneous and heterogeneous mixtures of peptides characterized by the above-mentioned properties may form stable macroscopic membranes, filaments, and hydrogels. Peptides which are self-complementary and self-compatible may form membranes, filaments, and hydrogels in a homogeneous mixture. Heterogeneous peptides, including those which cannot form membranes, filaments, and hydrogels in homogeneous solutions, which are complementary and/or structurally compatible with each other may also self-assemble into macroscopic membranes, filaments, and hydrogels.

The membranes, filaments, and hydrogels may be non-cytotoxic. The hydrogels of the present disclosure may be digested and metabolized in a subject. The hydrogels may be biodegraded in 30 days or less. They have a simple composition, are permeable, and are easy and relatively inexpensive to produce in large quantities. The membranes and filaments, hydrogels or scaffolds may also be produced and stored in a sterile condition. The optimal lengths for membrane formation may vary with at least one of the amino acid composition, solution conditions, and conditions at the target site.

The amino acids of the self-assembling or amphiphilic peptides may be selected from d-amino acids, 1-amino acids, or combinations thereof. The hydrophobic amino acids may include Ala, Val, Ile, Met, Phe, Tyr, Trp, Ser, Thr and Gly. The hydrophilic amino acids may be basic amino acids, for example, Lys, Arg, His, Orn; acidic amino acids, for example, Glu, Asp, or amino acids which form hydrogen bonds, for example, Asn, Gln. Acidic and basic amino acids may be clustered on a peptide. The carboxyl and amino groups of the terminal residues may be protected or not protected. Membranes or hydrogels may be formed in a homogeneous mixture of self-complementary and self-compatible peptides or in a heterogeneous mixture of peptides which are complementary and structurally compatible to each other. Peptides fitting the above criteria may self-assemble into macroscopic membranes under suitable conditions, described herein.

The peptide may comprise or consist essentially of a sequence selected from the group consisting of: RADA (SEQ ID NO:1), IEIK (SEQ ID NO:2), TTTT (SEQ ID NO:3), ATAT (SEQ ID NO:4), TVTV (SEQ ID NO:5), ASAS (SEQ ID NO:6), SSSS (SEQ ID NO:7), VVVTTTT (SEQ ID NO:8), and combinations thereof. Other peptide sequences are contemplated and are within the scope of this disclosure. In certain embodiments, the peptide may comprise or consist essentially of a repeated sequence of arginine, alanine, and aspartic acid.

The peptides of the present disclosure may include peptides having the repeating sequence of arginine, alanine, aspartic acid and alanine (Arg-Ala-Asp-Ala (RADA) (SEQ ID NO:1)), and such peptide sequences may be represented by (RADA)$_p$, wherein p=2-50.

Other peptide sequences may be represented by self-assembling peptides having the repeating sequence of isoleucine, glutamic acid, isoleucine and lysine (Ile-Glu-Ile-Lys (IEIK) (SEQ ID NO:2)), and such peptide sequences are represented by (IEIK)$_p$, wherein p=2-50.

Other peptide sequences may be represented by self-assembling peptides having the repeating sequence of lysine, leucine, aspartic acid, and leucine (Lys-Leu-Asp-Leu (KLDL) (SEQ ID NO:9)), and such peptide sequences are represented by (KLDL)$_p$, wherein p=2-50. Other peptide sequences may be represented by self-assembling peptides having the repeating sequence of lysine, leucine, and aspartic acid (Lys-Leu-Asp (KLD) (SEQ ID NO:10)), and such peptide sequences are represented by (KLD)$_p$, wherein p=2-50. As specific examples of self-assembling peptides according to the invention there may be a self-assembling peptide RADA16 (SEQ ID NO:11) having the sequence Arg-Ala-Asp-Ala-Arg-Ala-Asp-Ala-Arg-Ala-Asp-Ala-Arg-Ala-Asp-Ala (RADA)$_4$ (SEQ ID NO:11), a self-assembling peptide IEIK13 (SEQ ID NO:12) having the sequence Ile-Glu-Ile-Lys-Ile-Glu-Ile-Lys-Ile-Glu-Ile-Lys-Ile (IEIK)$_3$I (SEQ ID NO:12), a self-assembling peptide IEIK17 (SEQ ID NO:13) having the sequence Ile-Glu-Ile-Lys-Ile-Glu-Ile-Lys-Ile-Glu-Ile-Lys-Ile-Glu-Ile-Lys-Ile (IEIK)$_4$I (SEQ ID NO:13) or a self-assembling peptide KLDL12 (SEQ ID NO:14) having the sequence Lys-Leu-Asp-Leu-Lys-Leu-Asp-Leu-Lys-Leu-Asp-Leu (KLDL)$_3$ (SEQ ID NO:14).

The criteria of amphiphilic sequence, length, complementarity and structural compatibility apply to heterogeneous mixtures of peptides. For example, two different peptides may be used to form the membranes: peptide A, Val-Arg-Val-Arg-Val-Asp-Val-Asp-Val-Arg-Val-Arg-Val-Asp-Val-Asp (VRVRVDVDVRVRVDVD) (SEQ ID NO:15) has Arg and Asp as the hydrophilic residues and peptide B, Ala-Asp-Ala-Asp-Ala-Lys-Ala-Lys-Ala-Asp-Ala-Asp-Ala-Lys-Ala-Lys ADADADAKAKADADAKAK (SEQ ID NO:16), has Lys and Asp. Peptides A and B are complementary; the Arg on A can form an ionized pair with the Asp on B and the Asp on A can form an ionized pair with the Lys on B. Thus, in a heterogeneous mixture of peptides A and B, membranes would likely form, but they would be homogeneously composed of either peptide A or B.

Membranes and hydrogels can also be formed of heterogeneous mixtures of peptides, each of which alone would not form membranes, if they are complementary and structurally compatible to each other. For example, mixtures of (Lys-Ala-Lys-Ala)$_4$ (KAKA)$_4$ (SEQ ID NO:17) and (Glu-Ala-Glu-Ala)$_4$ (EAEA)$_4$ (SEQ ID NO:18) or of (Lys-Ala-Lys-Ala)$_4$ (KAKA)$_4$ (SEQ ID NO:17) and (Ala-Asp-Ala-Asp)$_4$ (ADAD)$_4$ (SEQ ID NO:19) would be expected to form membranes, but not any of these peptides alone due to lack of complementarity.

Peptides, which are not perfectly complementary or structurally compatible, can be thought of as containing mismatches analogous to mismatched base pairs in the hybridization of nucleic acids. Peptides containing mismatches can form membranes if the disruptive force of the mismatched pair is dominated by the overall stability of the interpeptide interaction. Functionally, such peptides can also be considered as complementary or structurally compatible. For example, a mismatched amino acid pair may be tolerated if it is surrounded by several perfectly matched pairs on each side.

Each of the peptide sequences disclosed herein may provide for peptides comprising, consisting essentially of, and consisting of the amino acid sequences recited.

The present disclosure provides materials, methods, and kits for solutions, hydrogels, and scaffolds comprising, consisting essentially of, or consisting of the peptides recited herein.

A 1 weight per volume (w/v) percent aqueous (water) solution and a 2.5 w/v percent of (RADA)$_4$ (SEQ ID NO:11) is available as the product PuraMatrix™ peptide hydrogel by 3-D Matrix, Ltd.

Certain peptides may contain sequences which are similar to the cell attachment ligand RGD (Arginine-Glycine-Aspartic acid). The suitability of these peptides for supporting in vitro cell growth was tested by introducing a variety of cultured primary and transformed cells to homopolymer sheets of Ala-Glu-Ala-Glu-Ala-Lys-Ala-Lys-Ala-Glu-Ala-Glu-Ala-Lys-Ala-Lys (AEAEAKAKAEAEAKAK (EAK16) (SEQ ID NO:20)), RAD16 (SEQ ID NO:21), RADA16 (SEQ ID NO:11), and heteropolymers of RAD16 (SEQ ID NO:21) and EAK16 (SEQ ID NO:20). The RAD-based peptides may be of particular interest because the similarity of this sequence to RGD. The RAD sequence is a high affinity ligand present in the extracellular matrix protein tenascin and is recognized by integrin receptors. The EAK16 (SEQ ID NO:20) peptide and other peptides disclosed herein were derived from a region of a yeast protein, zuotin.

A list of peptides that may form membranes, hydrogels or scaffolds in homogeneous or heterogeneous mixtures are listed in Table 1.

TABLE 1

Potential hydrogel-forming peptides

| NAME | SEQUENCE (N→C) | SEQ ID NO |
|---|---|---|
| RADA | RADA | SEQ ID NO: 1 |
| IEIK | IEIK | SEQ ID NO: 2 |
| TTTT | TTTT | SEQ ID NO: 3 |
| ATAT | ATAT | SEQ ID NO: 4 |
| TVTV | TVTV | SEQ ID NO: 5 |

TABLE 1-continued

Potential hydrogel-forming peptides

| NAME | SEQUENCE (N→C) | SEQ ID NO |
|---|---|---|
| ASAS | ASAS | SEQ ID NO: 6 |
| SSSS | SSSS | SEQ ID NO: 7 |
| VVVTTTT | VVVTTTT | SEQ ID NO: 8 |
| KLDL | KLDL | SEQ ID NO: 9 |
| KLD | KLD | SEQ ID NO: 10 |
| (RADA)$_4$ | RADARADARADARADA | SEQ ID NO: 11 |
| (IEIK)$_3$I | IEIKIEIKIEIKI | SEQ ID NO: 12 |
| (IEIK)$_4$I | IEIKIEIKIEIKIEIKI | SEQ ID NO: 13 |
| (KLDL)$_3$ | KLDLKLDLKLDL | SEQ ID NO: 14 |
| Peptide A | VRVRVDVDVRVRVDVD | SEQ ID NO: 15 |
| Peptide B | ADADAKAKADADAKAK | SEQ ID NO: 16 |
| (KAKA)$_4$ | KAKAKAKAKAKAKAKA | SEQ ID NO: 17 |
| (EAEA)$_4$ | EAEAEAEAEAEAEAEA | SEQ ID NO: 18 |
| (ADAD)$_4$ | ADADADADADADADAD | SEQ ID NO: 19 |
| EAK16 | AEAEAKAKAEAEAKAK | SEQ ID NO: 20 |
| RAD16 | ARADARADARADARAD | SEQ ID NO: 21 |
| KAKA16 | KAKAKAKAKAKAKAKA | SEQ ID NO: 22 |
| KAKA5 | KAKAK | SEQ ID NO: 23 |
| KAE16 | AKAKAEAEAKAKAEAE | SEQ ID NO: 24 |
| AKE16 | AKAEAKAEAKAEAKAE | SEQ ID NO: 25 |
| EKA16 | EAKAEAKAEAKAEAKA | SEQ ID NO: 26 |
| EAK8 | AEAEAKAK | SEQ ID NO: 27 |
| EAK12 | AEAKAEAEAKAK | SEQ ID NO: 28 |
| KEA16 | KAEAKAEAKAEAKAEA | SEQ ID NO: 29 |
| AEK16 | AEAKAEAKAEAKAEAK | SEQ ID NO: 30 |
| ARD8 | ARARADAD | SEQ ID NO: 31 |
| DAR16 | ADADARARADADARAR | SEQ ID NO: 32 |
| RAD16 | ARADARADARADARAD | SEQ ID NO: 33 |
| DRA16 | DARADARADARADARA | SEQ ID NO: 34 |
| ADR16 | ADARADARADARADAR | SEQ ID NO: 35 |
| ARA16 | ARARADADARARADAD | SEQ ID NO: 36 |
| ARDAKE16 | ARADAKAEARADAKAE | SEQ ID NO: 37 |
| AKEW16 | AKAEARADAKAEARAD | SEQ ID NO: 38 |
| ARKADE16 | ARAKADAEARAKADAE | SEQ ID NO: 39 |
| AKRAED16 | AKARAEADAKARADAE | SEQ ID NO: 40 |
| AQ16 | AQAQAQAQAQAQAQAQ | SEQ ID NO: 41 |
| VQ16 | VQVQVQVQVQVQVQVQ | SEQ ID NO: 42 |
| YQ16 | YQYQYQYQYQYQYQYQ | SEQ ID NO: 43 |

TABLE 1-continued

Potential hydrogel-forming peptides

| NAME | SEQUENCE (N→C) | SEQ ID NO |
|---|---|---|
| HQ16 | HQHQHQHQHQHQHQHQ | SEQ ID NO: 44 |
| AN16 | ANANANANANANANAN | SEQ ID NO: 45 |
| VN16 | VNVNVNVNVNVNVNVN | SEQ ID NO: 46 |
| YN16 | YNYNYNYNYNYNYNYN | SEQ ID NO: 47 |
| HN16 | HNHNHNHNHNHNHNHN | SEQ ID NO: 48 |
| ANQ16 | ANAQANAQANAQANAQ | SEQ ID NO: 49 |
| AQN16 | AQANAQANAQANAQAN | SEQ ID NO: 50 |
| VNQ16 | VNVQVNVQVNVQVNVQ | SEQ ID NO: 51 |
| VQK16 | VQVNVQVNVQVNVQVN | SEQ ID NO: 52 |
| YNQ16 | YNYQYNYQYNYQYNYQ | SEQ ID NO: 53 |
| YQN16 | YQYNYQYNYQYNYQYN | SEQ ID NO: 54 |
| HNQ16 | HNHQHNHQHNHQHNHQ | SEQ ID NO: 55 |
| HQN16 | HQHNHQHNHQHNHQHN | SEQ ID NO: 56 |
| AKQD18 | AKAQADAKAQADAKAQAD | SEQ ID NO: 57 |
| VKQ18 | VKVQVDVKVQVDVKVQVD | SEQ ID NO: 58 |
| YKQ18 | YKYQYDYKYQYDYKYQYD | SEQ ID NO: 59 |
| HKQ18 | HKHQHDHKHQHDHKHQHD | SEQ ID NO: 60 |
| RAD | RAD | SEQ ID NO: 61 |
| AAAAAAK | AAAAAAK | SEQ ID NO: 62 |
| AAAAAAD | AAAAAAD | SEQ ID NO: 63 |
| TTTTTTT | TTTTTTT | SEQ ID NO: 64 |
| ATATATAT | ATATATAT | SEQ ID NO: 65 |
| TVTVTVTV | TVTVTVTV | SEQ ID NO: 66 |
| ASASASAS | ASASASAS | SEQ ID NO: 67 |
| SSSSSSS | SSSSSSS | SEQ ID NO: 68 |
| (RADA)$_{50}$ | RADARADARADARADARADARADARADARADARADARADA DARADARADARADARADARADARADARADARADARADA RADARADARADARADARADARADARADARADARADARADA DARADARADARADARADARADARADARADARADARADA RADARADARADARADARADARADARADA RADARADARADARADARADARADARADARADARADARADA DARADA | SEQ ID NO: 69 |
| (IEIK)$_{50}$ | IEIKIEIKIEIKIEIKIEIKIEIKIEIKIEIKIEIKIEIK IEIKIEIKIEIKIEIKIEIKIEIKIEIKIEIKIEIKIEIK IEIKIEIKIEIKIEIKIEIKIEIKIEIKIEIKIEIKIEIK IEIKIEIKIEIKIEIKIEIKIEIKIEIKIEIKIEIKIEIK IEIKIEIK | SEQ ID NO: 70 |
| (IEIK)$_{50}$I | IEIKIEIKIEIKIEIKIEIKIEIKIEIKIEIKIEIKIEIK IEIKIEIKIEIKIEIKIEIKIEIKIEIKIEIKIEIKIEIK IEIKIEIKIEIKIEIKIEIKIEIKIEIKIEIKIEIKIEIK IEIKIEIKIEIKIEIKIEIKIEIKIEIKIEIKIEIKIEIK IEIKIEIKI | SEQ ID NO: 71 |
| (KLDL)$_{50}$ | KLDLKLDLKLDLKLDLKLDLKLDLKLDLKLDL KLDLKLDLKLDLKLDLKLDLKLDLKLDLKLDL KLDLKLDLKLDLKLDLKLDLKLDLKLDLKLDL KLDLKLDLKLDLKLDLKLDLKLDLKLDLKLDL KLDLKLDLKLDLKLDLKLDLKLDLKLDLKLDL KLDLKLDLKLDLKLDLKLDLKLDL | SEQ ID NO: 72 |

TABLE 1-continued

Potential hydrogel-forming peptides

| NAME | SEQUENCE (N→C) | SEQ ID NO |
|---|---|---|
| (KLD) | KLDKLDKLDKLDKLDKLDKLDKLDKLDKLDKL<br>DKLDKLDKLDKLDKLDKLDKLDKLDKLDKLDK<br>LDKLDKLDKLDKLDKLDKLDKLDKLDKLDKLD<br>KLDKLDKLDKLDKLDKLDKLDKLDKLDKLDKL<br>DKLDKLDKLD | SEQ ID NO: 73 |
| (KLDL)$_2$ | KLDLKLDL | SEQ ID NO: 74 |
| (KLDL)$_3$ | KLDLKLDLKLDL | SEQ ID NO: 75 |
| (AGAG)$_4$ | AGAGAGAGAGAGAGAG | SEQ ID NO: 76 |
| (LALA)$_4$ | LALALALALALALALA | SEQ ID NO: 77 |
| LALAL | LALAL | SEQ ID NO: 78 |
| (ALALAGAG)$_2$ | ALALAGAGALALAGAG | SEQ ID NO: 79 |
| (ALAG)$_4$ | ALAGALAGALAGALAG | SEQ ID NO: 80 |
| (GALA)$_4$ | GALAGALAGALAGALA | SEQ ID NO: 81 |
| AGAGALAL | AGAGALAL | SEQ ID NO: 82 |
| AGALAGAGALAL | AGALAGAGALAL | SEQ ID NO: 83 |
| (LAGA)$_4$ | LAGALAGALAGALAGA | SEQ ID NO: 84 |
| (AGAL)$_4$ | AGALAGALAGALAGAL | SEQ ID NO: 85 |

Without wishing to be bound by any particular theory, it is believed that the self-assembly of the peptides may be attributable to hydrogen bonding and hydrophobic bonding between the peptide molecules by the amino acids composing the peptides.

As used herein, an "effective amount" or a "therapeutically effective amount" refers to an amount of a peptide, peptide solution or hydrogel effective to prevent or mitigate biological tissue adhesion in a subject. In certain embodiments, such an "effective amount" or "therapeutically effective amount" may refer to an amount of a peptide, peptide solution or hydrogel which is effective, upon single or multiple administration (application or injection) to a subject, in treating, or in curing, alleviating, relieving or improving a subject with a disorder beyond that expected in the absence of such treatment. This may include a particular concentration or range of concentrations of peptide in the peptide solution or hydrogel and additionally, or in the alternative, a particular volume or range of volumes of the peptide solution or hydrogel. The method of facilitating may comprise providing instructions to prepare at least one of the effective amount and the effective concentration.

The self-assembling peptides of the present disclosure, such as RADA16 (SEQ ID NO:11), may be peptide sequences that lack a distinct physiologically or biologically active motif or sequence, and therefore may not impair intrinsic cell function. Physiologically active motifs may control numerous intracellular phenomena such as transcription, and the presence of physiologically active motifs may lead to phosphorylation of intracytoplasmic or cell surface proteins by enzymes that recognize the motifs. When a physiologically active motif is present in a peptide tissue anti-adhesion agent, transcription of proteins with various functions may be activated or suppressed. The self-assembling peptides, of the present disclosure may lack such physiologically active motifs and therefore do not carry this risk.

The optimal lengths for membrane formation may vary with the amino acid composition. A stabilization factor contemplated by the peptides of the present disclosure is that complementary peptides maintain a constant distance between the peptide backbones. Peptides which can maintain a constant distance upon pairing are referred to herein as structurally compatible. The interpeptide distance can be calculated for each ionized or hydrogen bonding pair by taking the sum of the number of unbranched atoms on the side-chains of each amino acid in the pair. For example, lysine has 5 and glutamic acid has 4 unbranched atoms on its side-chains, respectively.

The dosage, for example, volume or concentration, administered (for example, applied or injected) may vary depending upon the form of the peptide (for example, in a peptide solution, hydrogel, or in a dried form, such as a lyophilized form) and the route of administration utilized. The exact formulation, route of administration, volume, and concentration can be chosen in view of the subject's condition and in view of the particular target area or location that the peptide solution, hydrogel, or other form of peptide will be administered. Lower or higher doses than those recited herein may be used or required. Specific dosage and treatment regimens for any particular subject may depend upon a variety of factors, which may include the specific peptide or peptides employed, the dimension of the area that is being treated, the desired thickness of the resulting hydrogel that may be positioned in the desired target area, and the length of time of treatment. Other factors that may affect the specific dosage and treatment regimens include age, body weight, general health status, sex, time of administration, rate of degradation, the severity and course of the disease, condition or symptoms, and the judgment of the treating physician. In certain embodiments, the peptide solution may be administered in a single dose. In other embodiments, the peptide solution may be administered in more than one dose, or multiple doses. The peptide solution may be administered in at least two doses.

An effective amount and an effective concentration of the peptide solution may be selected to at least partially provide or promote anti-adhesion, e.g., prevent or mitigate biological tissue adhesion. In some embodiments, at least one of the effective amount and the effective concentration may be based in part on a dimension or diameter of the target area. In other embodiments, at least one of the effective amount and the effective concentration is based in part on the flow rate of one or more fluids at or near the target area.

The effective amount may include volumes of from about 0.1 milliliters (mL) to about 100 mL of a peptide solution. The effective amount may include volumes of from about 0.1 mL to about 10 mL of a peptide solution. In certain embodiments, the effective amount may be about 0.5 mL. In other embodiments, the effective amount may be about 1.0 mL. In yet other embodiments, the effective amount may be about 1.5 mL. In still yet other embodiments, the effective amount may be about 2.0 mL. In some other embodiments, the effective amount may be about 3.0 mL.

In certain embodiments, the effective amount may be approximately 0.1 mL per 1 $cm^2$ to approximately 5 mL per 1 $cm^2$ of target area. In certain embodiments, the effective amount may be approximately 1 mL per 1 $cm^2$ of target area. This effective amount may be used related to a concentration, such as a 2.5 weight per volume percent of a peptide solution of the present disclosure.

The effective concentration may be, as described herein, an amount that may provide for or promote anti-adhesion, e.g., prevent or mitigate biological tissue adhesion. Various properties at or near the target site may contribute to the selection or determination of the effective concentration including at least one of a dimension or diameter of the target area, and the flow rate of one or more fluids at or near the target area.

The effective concentration may include peptide concentrations in the solution in a range of about 0.1 weight per volume (w/v) percent to about 10 w/v percent. The effective concentration may include peptide concentrations in the solution in a range of about 0.1 w/v percent to about 3.5 w/v percent. In certain embodiments, the effective concentration may be about 1 w/v percent. In other embodiments, the effective concentration may be about 2.5 w/v percent. In yet other embodiments, the effective concentration may be about 3.0 w/v percent.

In certain embodiments, a peptide solution having a higher concentration of peptide may provide for a more effective hydrogel that has the ability to stay in place and provide effective, or promote anti-adhesion, e.g., prevent or mitigate biological tissue adhesion. For purposes of delivering the peptide solution, higher concentrations of peptide solutions may become too viscous to allow for effective and selective administration of the solution. It is possible that if a high enough concentration is not selected, the hydrogel may not be effective in the target area for the desired period of time.

The effective concentration may be selected to provide for a solution that may be administered by injection or other means using a particular diameter or gauge catheter or needle.

Methods of the disclosure contemplate single as well as multiple administrations of a therapeutically effective amount of the peptides, compositions, peptide solutions, membranes, filaments, and hydrogels as described herein. Peptides as described herein may be administered at regular intervals, depending on the nature, severity and extent of the subject's condition. In some embodiments, a peptide, composition, peptide solution, membrane, filament, or hydrogel may be administered in a single administration. In some embodiments, a peptide, composition, peptide solution, or hydrogel described herein is administered in multiple administrations. In some embodiments, a therapeutically effective amount of a peptide, composition, peptide solution, membrane, filament, or hydrogel may be administered periodically at regular intervals. The regular intervals selected may be based on any one or more of the initial peptide concentration of the solution administered, the amount administered, and the degradation rate of the hydrogel formed. For example, after an initial administration, a follow-on administration may occur after, for example, one week, two weeks, four weeks, six weeks, or eight weeks. The follow-on administration may comprise administration of a solution having the same concentration of peptide and volume as the initial administration, or may comprise administration of a solution of lesser or great concentration of peptide and volume. The selection of the appropriate follow-on administration of peptide solution may be based on imaging the target area and the area surrounding the target area and ascertaining the needs based on the condition of the subject. The pre-determined intervals may be the same for each follow-on administration, or they may be different. In some embodiments, a peptide, peptide solution, or hydrogel may be administered chronically at pre-determined intervals to maintain at least a partial anti-adhesion, e.g., prevention or mitigation of biological tissue adhesion, in a subject over the life of the subject. The pre-determined intervals may be the same for each follow-on administration, or they may be different. This may be dependent on whether the hydrogel formed from the previous administration is partially or totally disrupted or degraded. The follow-on administration may comprise administration of a solution having the same concentration of peptide and volume as the initial administration, or may comprise administration of a solution of lesser or great concentration of peptide and volume. The selection of the appropriate follow-on administration of peptide solution may be based on imaging the target area and the area surrounding the target area and ascertaining the needs based on the condition of the subject.

The peptides can be chemically synthesized or they can be purified from natural and recombinant sources. Using chemically synthesized peptides may allow the peptide solutions to be deficient in unidentified components such as unidentified components derived from the extracellular matrix of another animal. This property therefore may eliminate concerns of infection, including risk of viral infection compared to conventional tissue-derived biomaterials. This may eliminate concerns of infection including infections such as bovine spongiform encephalopathy (BSE), making the peptide highly safe for medical use.

The initial concentration of the peptide may be a factor in the size and thickness of the membrane, hydrogel, or scaffold formed. In general, the higher the peptide concentration, the higher the extent of membrane or hydrogel formation. Hydrogels, or scaffolds formed at higher initial peptide concentrations (about 10 mg/ml) (about 1.0 w/v percent) may be thicker and thus, likely to be stronger.

Formation of the, membranes, hydrogels, or scaffolds may be very fast, on the order of a few minutes. The formation of the membranes or hydrogels may be irreversible. In certain embodiments, the formation may be reversible, and in other embodiments, the formation may be irreversible. The hydrogel may form instantaneously upon administration to a target area. The formation of the hydrogel may occur within about one to two minutes of administration. In other examples, the formation of the hydrogel may occur within about three to four minutes of administration. In certain embodiments the time it takes to form the hydrogel may be based at least in part on one or more of the concentration of the peptide solution, the volume of peptide solution applied, and the conditions at the area of application or injection (for example, the concentration of monovalent metal cations at the area of application, the pH of the area, and the presence of one or more fluids at or near the area). The process may be unaffected by pH of less than or equal to 12, and by temperature. The membranes or hydrogels may form at temperatures in the range of 1 to 99 degrees Celsius.

The hydrogels may remain in position at the target area for a period of time sufficient to provide a desired effect using the methods and kits of the present disclosure. The desired effect using the methods and kits of the present disclosure may be to treat areas or to assist in healing of areas in which a surgical procedure at or near the site of a surgery was performed. For example, the desired effect using the methods and kits of the present disclosure may be to treat areas or to assist in healing of areas in which an endoscopic surgery is performed.

The period of time that the membranes or hydrogels may remain at the desired area may be for about 10 minutes. In certain examples, it may remain at the desired area for about 35 minutes. In certain further examples, it may remain at the desired area for one or more days, up to one or more weeks. In other examples, it may remain at the desired area for up to 30 days, or more. It may remain at the desired area indefinitely. In other examples, it may remain at the desired area for a longer period of time, until it is naturally degraded or intentionally removed. If the hydrogel naturally degrades over a period of time, subsequent application or injection of the hydrogel to the same or different location may be performed.

In certain embodiments, the self-assembling peptide may be prepared with one or more components that may provide for enhanced effectiveness of the self-assembling peptide or may provide another action, treatment, therapy, or otherwise interact with one or more components of the subject. For example, additional peptides comprising one or more biologically or physiologically active amino acid sequences or motifs may be included as one of the components along with the self-assembling peptide. Other components may include biologically active compounds such as a drug or other treatment that may provide some benefit to the subject. For example, a cancer treating drug or anticancer drug may be administered with the self-assembling peptide, or may be administered separately.

The peptide, peptide solution, or hydrogel may comprise small molecular drugs to treat the subject or to prevent hemolysis, inflammation, and infection. The small molecular drugs may be selected from the group consisting of glucose, saccharose, purified saccharose, lactose, maltose, trehalose, destran, iodine, lysozyme chloride, dimethylisoprpylazulene, tretinoin tocoferil, povidone iodine, alprostadil alfadex, anise alcohol, isoamyl salicylate, $\alpha,\alpha$-dimethylphenylethyl alcohol, bacdanol, helional, sulfazin silver, bucladesine sodium, alprostadil alfadex, gentamycin sulfate, tetracycline hydrochloride, sodium fusidate, mupirocin calcium hydrate and isoamyl benzoate. Other small molecular drugs may be contemplated. Protein-based drugs may be included as a component to be administered, and may include erythropoietin, tissue type plasminogen activator, synthetic hemoglobin and insulin.

A component may be included to protect the peptide solution against rapid or immediate formation into a hydrogel. This may include an encapsulated delivery system that may degrade over time to allow a controlled time release of the peptide solution into the target area to form the hydrogel over a desired, predetermined period of time. Biodegradable, biocompatible polymers may be used, such as ethylene vinyl acetate, polyanhydrides, polyglycolic acid, collagen, polyorthoesters, and polylactic acid.

In some embodiments, sugar may be added to the self-assembling peptide solution to improve the osmotic pressure of the solution from hypotonicity to isotonicity without reducing the tissue anti-adhesion effect, thereby allowing the biological safety to be increased. In certain examples, the sugar may be sucrose or glucose.

Any of the components described herein may be included in the peptide solution or may be administered separate from the peptide solution. Additionally, any of the methods and methods of facilitating provided herein may be performed by one or more parties.

A peptide, peptide solution, or hydrogel of the disclosure may be provided in a kit. Instructions for administering the solution to a target area of a subject may also be provided in the kit. The peptide solution may comprise a self-assembling peptide comprising at least about 7 amino acids in an effective amount and in an effective concentration to form a hydrogel to at least partially mitigate adhesion to a biological tissue. The peptide solution may comprise a self-assembling peptide comprising between about 7 amino acids to about 32 amino acids in an effective amount and in an effective concentration to form a hydrogel to at least partially mitigate adhesion to a biological tissue. The instructions for administering the solution may comprise methods for administering the peptide, peptide solution, or hydrogel provided herein, for example, by a route of administration described herein, at a dose, volume or concentration, or administration schedule. The peptide may be amphiphilic and at least a portion of the peptide may alternate between a hydrophobic amino acid and a hydrophilic amino acid.

The kit may also comprise informational material. The informational material may be descriptive, instructional, marketing or other material that relates to the methods described herein. In one embodiment, the informational material may include information about production of the peptide, peptide solution, or hydrogel disclosed herein, physical properties of the peptide, composition, peptide solution or hydrogel, concentration, volume, size, dimensions, date of expiration, and batch or production site.

The kit may also optionally include a device or materials to allow for administration of the peptide or peptide solution to the desired area. For example, a syringe, pipette, catheter, or other needle-based device may be included in the kit. Additionally, or alternatively, the kit may include a guidewire, endoscope, or other accompanying equipment to provide selective administration of the peptide solution to the target area.

The kit may comprise in addition to or in the alternative, other components or ingredients, such as components that may aid in positioning of the peptide solution, hydrogel or scaffold. Instructions may be provided in the kit to combine a sufficient quantity or volume of the peptide solution with a sucrose solution, that may or may not be provided with the kit. Instructions may be provided for diluting the peptide solution to administer an effective concentration of the solution to the target area. The instruction may describe diluting the peptide solution with a diluent or solvent. The diluent or solvent may be water. Instructions may further be provided for determining at least one of the effective concentration of the solution and the effective amount of the solution to the target area. This may be based on various parameters discussed herein, and may include the diameter of the lesion or wound at the target area.

Other components or ingredients may be included in the kit, in the same or different compositions or containers than the peptide, peptide solutions, or hydrogel. The one or more components that may include components that may provide for enhanced effectiveness of the self-assembling peptide or may provide another action, treatment, therapy, or otherwise interact with one or more components of the subject. For example, additional peptides comprising one or more biologically or physiologically active sequences or motifs may be included as one of the components along with the self-assembling peptide. Other components may include biologically active compounds such as a drug or other treatment that may provide some benefit to the subject. For example, a cancer treating drug or anticancer drug may be administered with the self-assembling peptide, or may be administered separately. The peptide, peptide solution, or hydrogel may comprise small molecular drugs to treat the subject or to prevent hemolysis, inflammation, and infection, as disclosed herein. A sugar solution such as a sucrose solution may be provided with the kit. The sucrose solution may be a 20% sucrose solution.

Other components which are disclosed herein may also be included in the kit.

In some embodiments, a component of the kit is stored in a sealed vial, for example, with a rubber or silicone closure (for example, a polybutadiene or polyisoprene closure). In some embodiments, a component of the kit is stored under inert conditions (for example, under nitrogen or another inert gas such as argon). In some embodiments, a component of the kit is stored under anhydrous conditions (for example, with a desiccant). In some embodiments, a component of the kit is stored in a light blocking container such as an amber vial.

As part of the kit or separate from a kit, syringes or pipettes may be pre-filled with a peptide, peptide solution, or hydrogel as disclosed herein. Methods to instruct a user to supply a self-assembling peptide solution to a syringe or pipette, with or without the use of other devices, and administering it to the target area through the syringe or pipette, with or without the use of other devices, is provided. Other devices may include, for example, a catheter with or without a guidewire.

In some embodiments of the disclosure, the self-assembling peptides may be used as a coating on a device or an instrument such as a stent or catheter, to suppress body fluid leakage. The self-assembling peptides may also be incorporated or secured to a support, such as gauze or a bandage, or a lining, that may provide a therapeutic effect to a subject, or that may be applied within a target area. The self-assembling peptides may also be soaked into a sponge for use.

The membranes may also be useful for culturing cell monolayers. Cells prefer to adhere to non-uniform, charged surfaces. The charged residues and conformation of the proteinaceous membranes promote cell adhesion and migration. The addition of growth factors, such as fibroblast growth factor, to the peptide membrane may further improve attachment, cell growth and neurite outgrowth.

Although the peptide solution may be liquid at acidic pH, the peptide may undergo self-organization or self-assembly upon adjustment of a pH level of the solution to a neutral or physiological pH level. The solution may be aqueous or non-aqueous.

The following examples are illustrative and not restrictive. Many variations of the technology will become apparent to those of skill in the art upon review of this disclosure. The scope of the technology should, therefore, be determined not with reference to the examples, but instead should be determined with reference to the appended claims along with their full scope of equivalents.

Example

Anti-adhesion methods utilizing self-assembling peptide solutions according to the present invention were assessed in a rabbit cecal-sidewall model, which is used to assess intra-abdominal adhesion formation and, more generally, anti-adhesion capacity.

The self-assembling peptide solution used in this example was PURASTAT® (3-D Matrix, Inc.), which is a commercial 2.5% solution of the RADA16 (SEQ ID NO:11) peptide. The test system was the rabbit, as follows:
Species: Rabbit (*Oryctolagus cuniculus*)
Strain: New Zealand White
Source: USDA licensed supplier
Sex: Female, nulliparous and nonpregnant
Body Weight Range: 4.0 to 6.0 kg at selection
Age: No particular age is prescribed for this test
Acclimation Period: Minimum 5 days
Number of Animals: Twenty One (+4 reserves)
Identification Method: Ear tag The rabbit is an appropriate model in numerous literature references for evaluating reduction of post-surgical adhesions. The rabbit represents the lowest sentient species that is physically large enough to accommodate the sidewall defects and the size of the implanted articles. The number of animals represented the smallest number that will yield interpretable results. Husbandry, Housing, and Environment Conditions conformed to NAMSA Standard Operating Procedures based on the "Guide for the Care and Use of Laboratory Animals." There are no available validated in vitro assays or computer-simulated models that can mimic the complexity of the rabbit model for post-surgical adhesion formation.

Methods. Pre-Operative Procedure: Within 2 days prior to the first surgical day, animals were weighed and randomly assigned by weight to treatment groups as indicated in Table 2.

TABLE 2

Cecal-Sidewall Model Animal Assignment

| Treatment Group | Number of Animals | Terminal Interval (±1 day) |
| --- | --- | --- |
| Surgical Control* | 5 | 14 days |
| Test Article Treated | 8 | |

*Surgical control group had the abrasion procedure, but no article was applied.

On the day of surgery, each animal was injected subcutaneously with 0.05 mg/kg of the analgesic buprenorphine and a fentanyl patch (analgesic; 25 µg/hr) was applied to an ear. Each animal was intramuscularly injected with a combination ketamine hydrochloride and xylazine (34 mg/kg+5 mg/kg) general anesthetic dosed at 0.6 mL/kg. A veterinary ophthalmic ointment was applied to both eyes of the animal to protect the corneas from drying. Each animal received a prophylactic dose of enrofloxacin (antibiotic) intramuscularly at 5.0 mg/kg. Each animal was clipped free of fur over the abdomen. The abdomen was scrubbed with a germicidal soap and wiped with 70% isopropyl alcohol. The surgical site was painted with an antiseptic such as povidone iodine and the animal was draped. Each animal was placed on isoflurane inhalant anesthetic for continued general anesthesia. The vital signs (temperature, heart rate, SPO2) of each animal was monitored during the procedure.

Operative Procedure. An approximate 12 cm in length skin incision was made along the midline of the ventral abdomen, beginning approximately 6 cm caudal to the xiphoid process. The abdominal wall was opened by incising along the linea alba. The entire cecum was exteriorized and abraded by wiping the entire serosal surface with a sterile dry gauze sponge until punctate bleeding was achieved. If the integrity of the cecal wall was compromised, the animal was euthanized and replaced. The cecum was repositioned in the abdomen. Bilateral defects measuring approximately 2×4.5 cm were made to the peritoneum over the abdominal sidewall. The defects were made approximately 4 cm lateral to the midline incision and approximately 7-9 cm caudal to the xiphoid process. An approximate 2×4.5 cm window of peritoneum was excised using sharp dissection and the muscle was disrupted by scraping the area with a scalpel blade to produce bleeding. If less than desirable bleeding is noted, additional bleeding will be induced by incising small blood vessels that are traversing through the defect area. Representative photographs were taken of the sidewall defect sites. For the test animals, the test article was applied to the peritoneal wall to cover and coat the sidewall defect sites. The defect sites remained untreated for the negative control group. The sidewall and cecum were returned to normal positioning and the abdominal wall was closed with a simple continuous suture pattern using appropriate absorbable suture. The subcutaneous tissue was closed with a simple continuous suture pattern using the same suture type. The skin was closed with 4-0 nonabsorbable suture, stainless steel wound clips, or a combination of these materials. The day of surgery was Day 0.

Post-Operative Observations. The animals were moved to a recovery area and placed on a heat source. Animals were monitored for recovery from the anesthetic. Once sternal recumbency was achieved, each animal was fitted with an Elizabethan collar and returned to its cage. Buprenorphine (SQ, 0.05 mg/kg) was administered approximately 6 hours after the initial dose. Enrofloxacin (IM, 5.0 mg/kg) was administered at the end of the day of surgery and then twice a day for the first 2 days after surgery.

At 14 (±1) days after surgery, the animals were weighed and euthanized by an intravenous injection of sodium pentobarbital based euthanasia solution. The peritoneal cavity was opened and the viscera were examined by a staff veterinarian. To maintain consistency in grading, the same veterinarian conducted all of the evaluations. The defect sites of each animal were photographed. Each site was examined for adhesion formation. Adhesions were graded for extent and strength as per the criteria shown in Tables 3 and 4:

TABLE 3

Adhesion Extent Scoring

| Score | Description |
| --- | --- |
| 0 | 0% |
| 1 | 1-25% |
| 2 | 26-50% |
| 3 | 51-75% |
| 4 | 76-100% |

TABLE 4

Adhesion Strength Scoring

| Score | Description |
| --- | --- |
| 0 | No adhesions present |
| 1 | Friable |
| 2 | Immature, easy to break |
| 3 | Mature, hard to break |

The general location of the adhesions and the tissue or organ involved in the adhesion was noted. Adhesions to the abdominal incision were noted and described as well as any other adhesions present within the abdominal cavity, however they were not scored.

Following scoring, the wounds and cecum were excised and placed in 10% neutral buffered formalin (NBF). Tissues was labeled with the animal number, wound identification, day of termination. No microscopic evaluation was conducted unless indicated by the Study Director.

Evaluation and Statistical Analysis. The mean scores for adhesion extent and strength and the incidence of adhesions were calculated. A total adhesion score (extent+strength of each defect) was calculated for each animal in the cecal-sidewall model. The scores for adhesion extent, adhesion strength, and total adhesion score were statistically compared. The mean and standard deviation was calculated for each parameter. Descriptive statistics and group comparisons data were accomplished using a validated statistical program. After screening the data for normality and equal variance, the appropriate parametric or nonparametric tests were performed. Normally distributed data with equal variance was considered parametric and compared using an unpaired t-test. If data was nonparametric, two sample t-test of unequal variance (Welch test) were conducted. Calculations resulting in probability (p) values less than 0.05 were considered statistically significant and appropriate post-hoc tests were run. For body weights, the mean and standard deviation was calculated for each treatment group.

Conclusions. Results are presented in Table 5A and 5B below. In the cecal sidewall model, 9/10 sites (5 animals total) formed adhesions in the surgical controls (See Table 5A) and only 4/16 sites (8 animals total) formed adhesions with self-assembling peptide solution treatment (See Table 5B). Preliminary statistical calculations demonstrate a significant difference (p-value=0.00126; result is significant at p<0.05) between the controls and PuraStat (SEQ ID NO:11) treated animals. In conclusion, the self-assembling peptide solution demonstrated anti-adhesive properties in the rabbit cecal side wall model.

TABLE 5A

Adhesions in Cecal Side Wall Model, Control Group

| Animal # | Control/ Test Article | Volume (mL) of Test Article (L/R) | Adhesions at Defect Site (L/R) | Adhesion Extent Score (L/R) | Adhesion Strength Score (L/R) | Additional Adhesions (Cecum to . . .) | Test Article Present | Incision Healing | Additional Comments |
|---|---|---|---|---|---|---|---|---|---|
| 17490 | Control | N/A | cecum and small intestine/ cecum | 1 & 1/4 | 2 & 1/2 | incision, omentum, cecum | no comment | yes | at time of explant, adhesion of cecum became adhered to left defect site |
| 17486 | Control | | cecum/ cecum | 4/2 | 2/2 | incision, cecum, omentum, large intestine | no comment | yes | |
| 17476 | Control | | non-abraded cecum & abraded cecum/ cecum & large intestine | 2 & 2/ 2 & 1 | 1 & 2/ 2 & 2 | incision, omentum, cecum, small intestine, abdominal fat | no comment | yes | |
| 17477 | Control | | none/ small intestine | 0/3 | 0/2 | sidewall (without defect), incision, small intestine, omentum, cecum, large intestine, (uterus to incision) | no comment | yes | |
| 17472 | Control | | cecum/ cecum (X2) | 4/1 & 1 | 2/2 & 2 | incision, cecum, large intestine | no comment | yes | non-abraded cecum to right sidewall defect |

TABLE 5B

Adhesions in Cecal Side-Wall Model, Self-Assembling Peptide Solution Treatment Group

| Animal # | Control/ Test Article | Volume (mL) of Test Article (L/R) | Adhesions at Defect Site (L/R) | Adhesion Extent Score (L/R) | Adhesion Strength Score (L/R) | Additional Adhesions (Cecum to . . .) | Test Article Present | Incision Healing | Additional Comments |
|---|---|---|---|---|---|---|---|---|---|
| 17484 | Test Article | 6/9 | none/ none | 0/0 | 0/0 | incision, omentum, cecum, large intestine | yes | yes | tan film adhered to surface of liver |
| 17485 | Test Article | 6/6 | none/ none | 0/0 | 0/0 | incision, large intestine, small intestine, cecum | yes | yes | tan film adhered to surface of the liver and spleen |
| 17482 | Test Article | 3/3 | cecum/ none | 4/0 | 2/0 | cecum, small intestine, abdominal fat, omentum | no | yes | small intestine adhered to incision |
| 17479 | Test Article | 3/3 | none/ none | 0/0 | 0/0 | omentum, cecum, large intestine | yes | yes | tan film (minimal) adhered to surface of the liver |
| 17470 | Test Article | 3/3 | none/ none | 0/0 | 0/0 | incision, omentum, cecum, large intestine, small intestine | no | yes | |
| 17471 | Test Article | 8.5/5 | none/ none | 0/0 | 0/0 | incision, small intestine, omentum, large intestine | yes | yes | |
| 17467 | Test Article | 6/6 | none/ cecum | 0/1 | 0/2 | Incision, cecum | yes | yes | small intestine adhere to cecum; tan material adhered to liver surface |
| 17474 | Test Article | 6/6 | cecum/ cecum | 1/2 | 2/2 | incision, cecum, small intestine, large intestine, messentery | yes | yes | extensive cecum to cecum adhesions |

What is claimed is:

1. A method for mitigating adhesion to a target area of a biological tissue or between biological tissues using a self-assembling peptide solution, the method comprising:
   administering an effective amount of the self-assembling peptide solution to a biological tissue at a surgical site, wherein the self-assembling peptide comprises (RADA) 4 (SEQ ID NO:11);
   wherein the self-assembling peptide is about 2.5% w/v of the solution;
   wherein the self-assembling peptide solution forms a hydrogel under physiological conditions;
   wherein the hydrogel mitigates adhesion to the biological tissue or of another biological tissue to the biological tissue at a surgical site;
   wherein the hydrogel assists in healing of areas in which a surgical procedure was performed; and
   wherein the biological tissue is cecum.

2. The method of claim 1, wherein an effective amount of the self-assembling peptide solution is approximately 0.1 mL per 1 cm$^2$ to approximately 5 mL per 1 cm$^2$ of the target area.

3. The method of claim 2, wherein the effective amount of the self-assembling peptide solution is approximately 1 mL per 1 cm$^2$ of target area.

4. The method of claim 1, wherein the hydrogel is formed before administering the self-assembling peptide solution to the target area, or wherein the hydrogel is formed after administering the self-assembling peptide solution to said target area.

5. The method of claim 1, wherein the self-assembling peptide solution further comprises a biologically active agent.

6. The method of claim 1, wherein the self-assembling peptide solution is substantially free of cells and/or drugs.

7. The method of claim 1, wherein the self-assembling peptide solution is administered in vivo.

8. The method of claim 1, wherein the biological tissue is human tissue.

* * * * *

SEQUENCE LISTING

```
Sequence total quantity: 85
SEQ ID NO: 1                    moltype = AA  length = 4
FEATURE                         Location/Qualifiers
REGION                          1..4
                                note = Synthetic peptide
source                          1..4
                                mol_type = protein
                                organism = synthetic construct
SEQUENCE: 1
RADA                                                                            4

SEQ ID NO: 2                    moltype = AA  length = 4
FEATURE                         Location/Qualifiers
REGION                          1..4
                                note = Synthetic peptide
source                          1..4
                                mol_type = protein
                                organism = synthetic construct
SEQUENCE: 2
IEIK                                                                            4

SEQ ID NO: 3                    moltype = AA  length = 4
FEATURE                         Location/Qualifiers
REGION                          1..4
                                note = Synthetic peptide
source                          1..4
                                mol_type = protein
                                organism = synthetic construct
SEQUENCE: 3
TTTT                                                                            4

SEQ ID NO: 4                    moltype = AA  length = 4
FEATURE                         Location/Qualifiers
REGION                          1..4
                                note = Synthetic peptide
source                          1..4
                                mol_type = protein
                                organism = synthetic construct
SEQUENCE: 4
ATAT                                                                            4

SEQ ID NO: 5                    moltype = AA  length = 4
FEATURE                         Location/Qualifiers
REGION                          1..4
                                note = Synthetic peptide
source                          1..4
                                mol_type = protein
                                organism = synthetic construct
SEQUENCE: 5
TVTV                                                                            4

SEQ ID NO: 6                    moltype = AA  length = 4
FEATURE                         Location/Qualifiers
REGION                          1..4
                                note = Synthetic peptide
source                          1..4
                                mol_type = protein
                                organism = synthetic construct
SEQUENCE: 6
ASAS                                                                            4

SEQ ID NO: 7                    moltype = AA  length = 4
FEATURE                         Location/Qualifiers
REGION                          1..4
                                note = Synthetic Peptide
source                          1..4
                                mol_type = protein
                                organism = synthetic construct
SEQUENCE: 7
SSSS                                                                            4

SEQ ID NO: 8                    moltype = AA  length = 7
FEATURE                         Location/Qualifiers
REGION                          1..7
                                note = Synthetic peptide
source                          1..7
                                mol_type = protein
                                organism = synthetic construct
```

```
SEQUENCE: 8
VVVTTTT                                                                 7

SEQ ID NO: 9         moltype = AA  length = 4
FEATURE              Location/Qualifiers
REGION               1..4
                     note = Synthetic peptide
source               1..4
                     mol_type = protein
                     organism = synthetic construct
SEQUENCE: 9
KLDL                                                                    4

SEQ ID NO: 10        moltype =    length =
SEQUENCE: 10
000

SEQ ID NO: 11        moltype = AA  length = 16
FEATURE              Location/Qualifiers
REGION               1..16
                     note = Synthetic peptide
source               1..16
                     mol_type = protein
                     organism = synthetic construct
SEQUENCE: 11
RADARADARA DARADA                                                      16

SEQ ID NO: 12        moltype = AA  length = 13
FEATURE              Location/Qualifiers
REGION               1..13
                     note = Synthetic peptide
source               1..13
                     mol_type = protein
                     organism = synthetic construct
SEQUENCE: 12
IEIKIEIKIE IKI                                                         13

SEQ ID NO: 13        moltype = AA  length = 17
FEATURE              Location/Qualifiers
REGION               1..17
                     note = Synthetic peptide
source               1..17
                     mol_type = protein
                     organism = synthetic construct
SEQUENCE: 13
IEIKIEIKIE IKIEIKI                                                     17

SEQ ID NO: 14        moltype = AA  length = 12
FEATURE              Location/Qualifiers
REGION               1..12
                     note = Synthetic peptide
source               1..12
                     mol_type = protein
                     organism = synthetic construct
SEQUENCE: 14
KLDLKLDLKL DL                                                          12

SEQ ID NO: 15        moltype = AA  length = 16
FEATURE              Location/Qualifiers
REGION               1..16
                     note = Synthetic peptide
source               1..16
                     mol_type = protein
                     organism = synthetic construct
SEQUENCE: 15
VRVRVDVDVR VRVDVD                                                      16

SEQ ID NO: 16        moltype = AA  length = 16
FEATURE              Location/Qualifiers
REGION               1..16
                     note = Synthetic peptide
source               1..16
                     mol_type = protein
                     organism = synthetic construct
SEQUENCE: 16
ADADAKAKAD ADAKAK                                                      16

SEQ ID NO: 17        moltype = AA  length = 16
FEATURE              Location/Qualifiers
```

```
REGION                   1..16
                         note = Synthetic peptide
source                   1..16
                         mol_type = protein
                         organism = synthetic construct
SEQUENCE: 17
KAKAKAKAKA KAKAKA                                                         16

SEQ ID NO: 18            moltype = AA  length = 16
FEATURE                  Location/Qualifiers
REGION                   1..16
                         note = Synthetic peptide
source                   1..16
                         mol_type = protein
                         organism = synthetic construct
SEQUENCE: 18
EAEAEAEAEA EAEAEA                                                         16

SEQ ID NO: 19            moltype = AA  length = 16
FEATURE                  Location/Qualifiers
REGION                   1..16
                         note = Synthetic peptide
source                   1..16
                         mol_type = protein
                         organism = synthetic construct
SEQUENCE: 19
ADADADADAD ADADAD                                                         16

SEQ ID NO: 20            moltype = AA  length = 16
FEATURE                  Location/Qualifiers
REGION                   1..16
                         note = Synthetic peptide
source                   1..16
                         mol_type = protein
                         organism = synthetic construct
SEQUENCE: 20
AEAEAKAKAE AEAKAK                                                         16

SEQ ID NO: 21            moltype = AA  length = 16
FEATURE                  Location/Qualifiers
REGION                   1..16
                         note = Synthetic peptide
source                   1..16
                         mol_type = protein
                         organism = synthetic construct
SEQUENCE: 21
ARADARADAR ADARAD                                                         16

SEQ ID NO: 22            moltype = AA  length = 16
FEATURE                  Location/Qualifiers
REGION                   1..16
                         note = Synthetic peptide
source                   1..16
                         mol_type = protein
                         organism = synthetic construct
SEQUENCE: 22
KAKAKAKAKA KAKAKA                                                         16

SEQ ID NO: 23            moltype = AA  length = 5
FEATURE                  Location/Qualifiers
REGION                   1..5
                         note = Synthetic peptide
source                   1..5
                         mol_type = protein
                         organism = synthetic construct
SEQUENCE: 23
KAKAK                                                                      5

SEQ ID NO: 24            moltype = AA  length = 16
FEATURE                  Location/Qualifiers
REGION                   1..16
                         note = Synthetic peptide
source                   1..16
                         mol_type = protein
                         organism = synthetic construct
SEQUENCE: 24
AKAKAEAEAK AKAEAE                                                         16

SEQ ID NO: 25            moltype = AA  length = 16
```

```
FEATURE                 Location/Qualifiers
REGION                  1..16
                        note = Synthetic peptide
source                  1..16
                        mol_type = protein
                        organism = synthetic construct
SEQUENCE: 25
AKAEAKAEAK AEAKAE                                                               16

SEQ ID NO: 26           moltype = AA  length = 16
FEATURE                 Location/Qualifiers
REGION                  1..16
                        note = Synthetic peptide
source                  1..16
                        mol_type = protein
                        organism = synthetic construct
SEQUENCE: 26
EAKAEAKAEA KAEAKA                                                               16

SEQ ID NO: 27           moltype = AA  length = 8
FEATURE                 Location/Qualifiers
REGION                  1..8
                        note = Synthetic peptide
source                  1..8
                        mol_type = protein
                        organism = synthetic construct
SEQUENCE: 27
AEAEAKAK                                                                         8

SEQ ID NO: 28           moltype = AA  length = 12
FEATURE                 Location/Qualifiers
REGION                  1..12
                        note = Synthetic peptide
source                  1..12
                        mol_type = protein
                        organism = synthetic construct
SEQUENCE: 28
AEAKAEAEAK AK                                                                   12

SEQ ID NO: 29           moltype = AA  length = 16
FEATURE                 Location/Qualifiers
REGION                  1..16
                        note = Synthetic peptide
source                  1..16
                        mol_type = protein
                        organism = synthetic construct
SEQUENCE: 29
KAEAKAEAKA EAKAEA                                                               16

SEQ ID NO: 30           moltype = AA  length = 16
FEATURE                 Location/Qualifiers
REGION                  1..16
                        note = Synthetic peptide
source                  1..16
                        mol_type = protein
                        organism = synthetic construct
SEQUENCE: 30
AEAKAEAKAE AKAEAK                                                               16

SEQ ID NO: 31           moltype = AA  length = 8
FEATURE                 Location/Qualifiers
REGION                  1..8
                        note = Synthetic peptide
source                  1..8
                        mol_type = protein
                        organism = synthetic construct
SEQUENCE: 31
ARARADAD                                                                         8

SEQ ID NO: 32           moltype = AA  length = 16
FEATURE                 Location/Qualifiers
REGION                  1..16
                        note = Synthetic peptide
source                  1..16
                        mol_type = protein
                        organism = synthetic construct
SEQUENCE: 32
ADADARARAD ADARAR                                                               16
```

```
SEQ ID NO: 33           moltype = AA   length = 16
FEATURE                 Location/Qualifiers
REGION                  1..16
                        note = Synthetic peptide
source                  1..16
                        mol_type = protein
                        organism = synthetic construct
SEQUENCE: 33
ARADARADAR ADARAD                                                           16

SEQ ID NO: 34           moltype = AA   length = 16
FEATURE                 Location/Qualifiers
REGION                  1..16
                        note = Synthetic peptide
source                  1..16
                        mol_type = protein
                        organism = synthetic construct
SEQUENCE: 34
DARADARADA RADARA                                                           16

SEQ ID NO: 35           moltype = AA   length = 16
FEATURE                 Location/Qualifiers
REGION                  1..16
                        note = Synthetic peptide
source                  1..16
                        mol_type = protein
                        organism = synthetic construct
SEQUENCE: 35
ADARADARAD ARADAR                                                           16

SEQ ID NO: 36           moltype = AA   length = 16
FEATURE                 Location/Qualifiers
REGION                  1..16
                        note = Synthetic peptide
source                  1..16
                        mol_type = protein
                        organism = synthetic construct
SEQUENCE: 36
ARARADADAR ARADAD                                                           16

SEQ ID NO: 37           moltype = AA   length = 16
FEATURE                 Location/Qualifiers
REGION                  1..16
                        note = Synthetic peptide
source                  1..16
                        mol_type = protein
                        organism = synthetic construct
SEQUENCE: 37
ARADAKAEAR ADAKAE                                                           16

SEQ ID NO: 38           moltype = AA   length = 16
FEATURE                 Location/Qualifiers
REGION                  1..16
                        note = Synthetic peptide
source                  1..16
                        mol_type = protein
                        organism = synthetic construct
SEQUENCE: 38
AKAEARADAK AEARAD                                                           16

SEQ ID NO: 39           moltype = AA   length = 16
FEATURE                 Location/Qualifiers
REGION                  1..16
                        note = Synthetic peptide
source                  1..16
                        mol_type = protein
                        organism = synthetic construct
SEQUENCE: 39
ARAKADAEAR AKADAE                                                           16

SEQ ID NO: 40           moltype = AA   length = 16
FEATURE                 Location/Qualifiers
REGION                  1..16
                        note = Synthetic peptide
source                  1..16
                        mol_type = protein
                        organism = synthetic construct
SEQUENCE: 40
AKARAEADAK ARADAE                                                           16
```

```
SEQ ID NO: 41            moltype = AA  length = 16
FEATURE                  Location/Qualifiers
REGION                   1..16
                         note = Synthetic peptide
source                   1..16
                         mol_type = protein
                         organism = synthetic construct
SEQUENCE: 41
AQAQAQAQAQ AQAQAQ                                                         16

SEQ ID NO: 42            moltype = AA  length = 16
FEATURE                  Location/Qualifiers
REGION                   1..16
                         note = Synthetic peptide
source                   1..16
                         mol_type = protein
                         organism = synthetic construct
SEQUENCE: 42
VQVQVQVQVQ VQVQVQ                                                         16

SEQ ID NO: 43            moltype = AA  length = 16
FEATURE                  Location/Qualifiers
REGION                   1..16
                         note = Synthetic peptide
source                   1..16
                         mol_type = protein
                         organism = synthetic construct
SEQUENCE: 43
YQYQYQYQYQ YQYQYQ                                                         16

SEQ ID NO: 44            moltype = AA  length = 16
FEATURE                  Location/Qualifiers
REGION                   1..16
                         note = Synthetic peptide
source                   1..16
                         mol_type = protein
                         organism = synthetic construct
SEQUENCE: 44
HQHQHQHQHQ HQHQHQ                                                         16

SEQ ID NO: 45            moltype = AA  length = 16
FEATURE                  Location/Qualifiers
REGION                   1..16
                         note = Synthetic peptide
source                   1..16
                         mol_type = protein
                         organism = synthetic construct
SEQUENCE: 45
ANANANANAN ANANAN                                                         16

SEQ ID NO: 46            moltype = AA  length = 16
FEATURE                  Location/Qualifiers
REGION                   1..16
                         note = Synthetic peptide
source                   1..16
                         mol_type = protein
                         organism = synthetic construct
SEQUENCE: 46
VNVNVNVNVN VNVNVN                                                         16

SEQ ID NO: 47            moltype = AA  length = 16
FEATURE                  Location/Qualifiers
REGION                   1..16
                         note = Synthetic peptide
source                   1..16
                         mol_type = protein
                         organism = synthetic construct
SEQUENCE: 47
YNYNYNYNYN YNYNYN                                                         16

SEQ ID NO: 48            moltype = AA  length = 16
FEATURE                  Location/Qualifiers
REGION                   1..16
                         note = Synthetic peptide
source                   1..16
                         mol_type = protein
                         organism = synthetic construct
```

-continued

```
SEQUENCE: 48
HNHNHNHNHN HNHNHN                                                        16

SEQ ID NO: 49            moltype = AA  length = 16
FEATURE                  Location/Qualifiers
REGION                   1..16
                         note = Synthetic peptide
source                   1..16
                         mol_type = protein
                         organism = synthetic construct
SEQUENCE: 49
ANAQANAQAN AQANAQ                                                        16

SEQ ID NO: 50            moltype = AA  length = 16
FEATURE                  Location/Qualifiers
REGION                   1..16
                         note = Synthetic peptide
source                   1..16
                         mol_type = protein
                         organism = synthetic construct
SEQUENCE: 50
AQANAQANAQ ANAQAN                                                        16

SEQ ID NO: 51            moltype = AA  length = 16
FEATURE                  Location/Qualifiers
REGION                   1..16
                         note = Synthetic peptide
source                   1..16
                         mol_type = protein
                         organism = synthetic construct
SEQUENCE: 51
VNVQVNVQVN VQVNVQ                                                        16

SEQ ID NO: 52            moltype = AA  length = 16
FEATURE                  Location/Qualifiers
REGION                   1..16
                         note = Synthetic peptide
source                   1..16
                         mol_type = protein
                         organism = synthetic construct
SEQUENCE: 52
VQVNVQVNVQ VNVQVN                                                        16

SEQ ID NO: 53            moltype = AA  length = 16
FEATURE                  Location/Qualifiers
REGION                   1..16
                         note = Synthetic peptide
source                   1..16
                         mol_type = protein
                         organism = synthetic construct
SEQUENCE: 53
YNYQYNYQYN YQYNYQ                                                        16

SEQ ID NO: 54            moltype = AA  length = 16
FEATURE                  Location/Qualifiers
REGION                   1..16
                         note = Synthetic peptide
source                   1..16
                         mol_type = protein
                         organism = synthetic construct
SEQUENCE: 54
YQYNYQYNYQ YNYQYN                                                        16

SEQ ID NO: 55            moltype = AA  length = 16
FEATURE                  Location/Qualifiers
REGION                   1..16
                         note = Synthetic peptide
source                   1..16
                         mol_type = protein
                         organism = synthetic construct
SEQUENCE: 55
HNHQHNHQHN HQHNHQ                                                        16

SEQ ID NO: 56            moltype = AA  length = 16
FEATURE                  Location/Qualifiers
REGION                   1..16
                         note = Synthetic peptide
```

```
source                  1..16
                        mol_type = protein
                        organism = synthetic construct
SEQUENCE: 56
HQHNHQHNHQ HNHQHN                                                          16

SEQ ID NO: 57           moltype = AA  length = 18
FEATURE                 Location/Qualifiers
REGION                  1..18
                        note = Synthetic peptide
source                  1..18
                        mol_type = protein
                        organism = synthetic construct
SEQUENCE: 57
AKAQADAKAQ ADAKAQAD                                                        18

SEQ ID NO: 58           moltype = AA  length = 18
FEATURE                 Location/Qualifiers
REGION                  1..18
                        note = Synthetic peptide
source                  1..18
                        mol_type = protein
                        organism = synthetic construct
SEQUENCE: 58
VKVQVDVKVQ VDVKVQVD                                                        18

SEQ ID NO: 59           moltype = AA  length = 18
FEATURE                 Location/Qualifiers
REGION                  1..18
                        note = Synthetic peptide
source                  1..18
                        mol_type = protein
                        organism = synthetic construct
SEQUENCE: 59
YKYQYDYKYQ YDYKYQYD                                                        18

SEQ ID NO: 60           moltype = AA  length = 18
FEATURE                 Location/Qualifiers
REGION                  1..18
                        note = Synthetic peptide
source                  1..18
                        mol_type = protein
                        organism = synthetic construct
SEQUENCE: 60
HKHQHDHKHQ HDHKHQHD                                                        18

SEQ ID NO: 61           moltype =    length =
SEQUENCE: 61
000

SEQ ID NO: 62           moltype = AA  length = 7
FEATURE                 Location/Qualifiers
REGION                  1..7
                        note = Synthetic peptide
source                  1..7
                        mol_type = protein
                        organism = synthetic construct
SEQUENCE: 62
AAAAAAK                                                                     7

SEQ ID NO: 63           moltype = AA  length = 7
FEATURE                 Location/Qualifiers
REGION                  1..7
                        note = Synthetic peptide
source                  1..7
                        mol_type = protein
                        organism = synthetic construct
SEQUENCE: 63
AAAAAAD                                                                     7

SEQ ID NO: 64           moltype = AA  length = 7
FEATURE                 Location/Qualifiers
REGION                  1..7
                        note = Synthetic peptide
source                  1..7
                        mol_type = protein
                        organism = synthetic construct
SEQUENCE: 64
TTTTTTT                                                                     7
```

```
SEQ ID NO: 65          moltype = AA   length = 8
FEATURE                Location/Qualifiers
REGION                 1..8
                       note = Synthetic peptide
source                 1..8
                       mol_type = protein
                       organism = synthetic construct
SEQUENCE: 65
ATATATAT                                                                    8

SEQ ID NO: 66          moltype = AA   length = 8
FEATURE                Location/Qualifiers
REGION                 1..8
                       note = Synthetic peptide
source                 1..8
                       mol_type = protein
                       organism = synthetic construct
SEQUENCE: 66
TVTVTVTV                                                                    8

SEQ ID NO: 67          moltype = AA   length = 8
FEATURE                Location/Qualifiers
REGION                 1..8
                       note = Synthetic peptide
source                 1..8
                       mol_type = protein
                       organism = synthetic construct
SEQUENCE: 67
ASASASAS                                                                    8

SEQ ID NO: 68          moltype = AA   length = 7
FEATURE                Location/Qualifiers
REGION                 1..7
                       note = Synthetic peptide
source                 1..7
                       mol_type = protein
                       organism = synthetic construct
SEQUENCE: 68
SSSSSSS                                                                     7

SEQ ID NO: 69          moltype = AA   length = 200
FEATURE                Location/Qualifiers
REGION                 1..200
                       note = Synthetic peptide
VARIANT                9..200
                       note = "This sequence may encompass 2-50 'RADA' repeating
                        units"
REGION                 1..200
                       note = MISC_FEATURE - /note="Variant residues given in the
                        sequence have no preference with respect to those in the
                        annotations for variant positions"
source                 1..200
                       mol_type = protein
                       organism = synthetic construct
SEQUENCE: 69
RADARADARA DARADARADA RADARADARA DARADARADA RADARADARA DARADARADA    60
RADARADARA DARADARADA RADARADARA DARADARADA RADARADARA DARADARADA   120
RADARADARA DARADARADA RADARADARA DARADARADA RADARADARA DARADARADA   180
RADARADARA DARADARADA                                               200

SEQ ID NO: 70          moltype = AA   length = 200
FEATURE                Location/Qualifiers
REGION                 1..200
                       note = Synthetic peptide
VARIANT                9..200
                       note = "This sequence may emcompass 2-50 'IEIK' repeating
                        units"
REGION                 1..200
                       note = MISC_FEATURE - /note="Variant residues given in the
                        sequence have no preference with respect to those in the
                        annotations for variant positions"
source                 1..200
                       mol_type = protein
                       organism = synthetic construct
SEQUENCE: 70
IEIKIEIKIE IKIEIKIEIK IEIKIEIKIE IKIEIKIEIK IEIKIEIKIE IKIEIKIEIK    60
IEIKIEIKIE IKIEIKIEIK IEIKIEIKIE IKIEIKIEIK IEIKIEIKIE IKIEIKIEIK   120
```

```
IEIKIEIKIE IKIEIKIEIK IEIKIEIKIE IKIEIKIEIK IEIKIEIKIE IKIEIKIEIK    180
IEIKIEIKIE IKIEIKIEIK                                                 200

SEQ ID NO: 71           moltype = AA  length = 201
FEATURE                 Location/Qualifiers
REGION                  1..201
                        note = Synthetic peptide
VARIANT                 9..200
                        note = "This sequence may encompass 2-50 'IEIK' repeating
                         units"
REGION                  1..201
                        note = MISC_FEATURE - /note="Variant residues given in the
                         sequence have no preference with respect to those in the
                         annotations for variant positions"
source                  1..201
                        mol_type = protein
                        organism = synthetic construct
SEQUENCE: 71
IEIKIEIKIE IKIEIKIEIK IEIKIEIKIE IKIEIKIEIK IEIKIEIKIE IKIEIKIEIK    60
IEIKIEIKIE IKIEIKIEIK IEIKIEIKIE IKIEIKIEIK IEIKIEIKIE IKIEIKIEIK    120
IEIKIEIKIE IKIEIKIEIK IEIKIEIKIE IKIEIKIEIK IEIKIEIKIE IKIEIKIEIK    180
IEIKIEIKIE IKIEIKIEIK I                                              201

SEQ ID NO: 72           moltype = AA  length = 200
FEATURE                 Location/Qualifiers
REGION                  1..200
                        note = Synthetic peptide
REGION                  1..200
                        note = MISC_FEATURE - =note="Variant residues given in the
                         sequence have no preference with respect to those in the
                         annotations for variant positions"
source                  1..200
                        mol_type = protein
                        organism = synthetic construct
VARIANT                 9..200
                        note = "This sequence may encompass 2-50 'KLDL' repeating
                         units"
SEQUENCE: 72
KLDLKLDLKL DLKLDLKLDL KLDLKLDLKL DLKLDLKLDL KLDLKLDLKL DLKLDLKLDL    60
KLDLKLDLKL DLKLDLKLDL KLDLKLDLKL DLKLDLKLDL KLDLKLDLKL DLKLDLKLDL    120
KLDLKLDLKL DLKLDLKLDL KLDLKLDLKL DLKLDLKLDL KLDLKLDLKL DLKLDLKLDL    180
KLDLKLDLKL DLKLDLKLDL                                                 200

SEQ ID NO: 73           moltype = AA  length = 150
FEATURE                 Location/Qualifiers
REGION                  1..150
                        note = Synthetic peptide
REGION                  1..150
                        note = MISC_FEATURE - /note="Variant residues given in the
                         sequence have no preference with respect to those in the
                         annotations for variant positions"
source                  1..150
                        mol_type = protein
                        organism = synthetic construct
VARIANT                 7..150
                        note = "This sequence may encompass 2-50 'KLD' repeating
                         units"
SEQUENCE: 73
KLDKLDKLDKL DKLDKLDKLD KLDKLDKLDK LDKLDKLDKL DKLDKLDKLD              60
KLDKLDKLDK LDKLDKLDKL DKLDKLDKLD KLDKLDKLDK LDKLDKLDKL DKLDKLDKLD    120
KLDKLDKLDK LDKLDKLDKL DKLDKLDKLD                                     150

SEQ ID NO: 74           moltype = AA  length = 8
FEATURE                 Location/Qualifiers
REGION                  1..8
                        note = Synthetic peptide
source                  1..8
                        mol_type = protein
                        organism = synthetic construct
SEQUENCE: 74
KLDLKLDL                                                             8

SEQ ID NO: 75           moltype = AA  length = 12
FEATURE                 Location/Qualifiers
REGION                  1..12
                        note = Synthetic peptide
source                  1..12
                        mol_type = protein
                        organism = synthetic construct
```

```
SEQUENCE: 75
KLDLKLDLKL DL                                                          12

SEQ ID NO: 76           moltype = AA   length = 16
FEATURE                 Location/Qualifiers
REGION                  1..16
                        note = Synthetic peptide
source                  1..16
                        mol_type = protein
                        organism = synthetic construct
SEQUENCE: 76
AGAGAGAGAG AGAGAG                                                      16

SEQ ID NO: 77           moltype = AA   length = 16
FEATURE                 Location/Qualifiers
REGION                  1..16
                        note = Synthetic peptide
source                  1..16
                        mol_type = protein
                        organism = synthetic construct
SEQUENCE: 77
LALALALALA LALALA                                                      16

SEQ ID NO: 78           moltype = AA   length = 5
FEATURE                 Location/Qualifiers
REGION                  1..5
                        note = Synthetic peptide
source                  1..5
                        mol_type = protein
                        organism = synthetic construct
SEQUENCE: 78
LALAL                                                                   5

SEQ ID NO: 79           moltype = AA   length = 16
FEATURE                 Location/Qualifiers
REGION                  1..16
                        note = Synthetic peptide
source                  1..16
                        mol_type = protein
                        organism = synthetic construct
SEQUENCE: 79
ALALAGAGAL ALAGAG                                                      16

SEQ ID NO: 80           moltype = AA   length = 16
FEATURE                 Location/Qualifiers
REGION                  1..16
                        note = Synthetic peptide
source                  1..16
                        mol_type = protein
                        organism = synthetic construct
SEQUENCE: 80
ALAGALAGAL AGALAG                                                      16

SEQ ID NO: 81           moltype = AA   length = 16
FEATURE                 Location/Qualifiers
REGION                  1..16
                        note = Synthetic peptide
source                  1..16
                        mol_type = protein
                        organism = synthetic construct
SEQUENCE: 81
GALAGALAGA LAGALA                                                      16

SEQ ID NO: 82           moltype = AA   length = 8
FEATURE                 Location/Qualifiers
REGION                  1..8
                        note = Synthetic peptide
source                  1..8
                        mol_type = protein
                        organism = synthetic construct
SEQUENCE: 82
AGAGALAL                                                                8

SEQ ID NO: 83           moltype = AA   length = 12
FEATURE                 Location/Qualifiers
REGION                  1..12
                        note = Synthetic peptide
```

```
source              1..12
                    mol_type = protein
                    organism = synthetic construct
SEQUENCE: 83
AGALAGAGAL AL                                                              12

SEQ ID NO: 84       moltype = AA  length = 16
FEATURE             Location/Qualifiers
REGION              1..16
                    note = Synthetic peptide
source              1..16
                    mol_type = protein
                    organism = synthetic construct
SEQUENCE: 84
LAGALAGALA GALAGA                                                          16

SEQ ID NO: 85       moltype = AA  length = 16
FEATURE             Location/Qualifiers
REGION              1..16
                    note = Synthetic peptide
source              1..16
                    mol_type = protein
                    organism = synthetic construct
SEQUENCE: 85
AGALAGALAG ALAGAL                                                          16
```